United States Patent
Zambelli et al.

(10) Patent No.: US 9,545,393 B2
(45) Date of Patent: Jan. 17, 2017

(54) METHODS AND COMPOSITIONS FOR TREATING PAIN

(71) Applicant: The Board of Trustees of the Leland Stanford Junior University, Palo Alto, CA (US)

(72) Inventors: Vanessa Zambelli, Sao Paulo (BR); Che-Hong Chen, Fremont, CA (US); Daria Mochly-Rosen, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/423,674

(22) PCT Filed: Aug. 23, 2013

(86) PCT No.: PCT/US2013/056432
§ 371 (c)(1),
(2) Date: Feb. 24, 2015

(87) PCT Pub. No.: WO2014/031982
PCT Pub. Date: Feb. 27, 2014

(65) Prior Publication Data
US 2015/0182495 A1    Jul. 2, 2015

Related U.S. Application Data

(60) Provisional application No. 61/693,188, filed on Aug. 24, 2012.

(51) Int. Cl.
| | |
|---|---|
| *A61K 31/36* | (2006.01) |
| *A61P 23/00* | (2006.01) |
| *A61K 31/357* | (2006.01) |
| *A01K 67/027* | (2006.01) |
| *C12N 9/02* | (2006.01) |
| *C12N 15/85* | (2006.01) |

(52) U.S. Cl.
CPC ........... *A61K 31/36* (2013.01); *A01K 67/0278* (2013.01); *A61K 31/357* (2013.01); *C12N 9/0008* (2013.01); *C12N 15/8509* (2013.01); *C12Y 102/01003* (2013.01); *A01K 2217/077* (2013.01); *A01K 2227/105* (2013.01); *A01K 2267/0356* (2013.01)

(58) Field of Classification Search
CPC ..................................... A61K 31/36
USPC ................... 514/464, 466; 549/441
See application file for complete search history.

(56) References Cited

U.S. PATENT DOCUMENTS

| | | | |
|---|---|---|---|
| 2009/0082431 A1* | 3/2009 | Mochly-Rosen | C07D 405/12 514/466 |
| 2010/0098713 A1 | 4/2010 | Meyers et al. | |
| 2010/0113423 A1 | 5/2010 | Mochly-Rosen et al. | |

OTHER PUBLICATIONS

Definition of prevent, Princeton University "About WordNet." WordNet. Princeton University. 2010. <http://wordnet.princeton.edu> accessed Sep. 18, 2012.*
Foulkes et al. PLOS Genetics 2008, 4 (7), e1000086, p. 1-9.*
Basbaum et al. Cell 2009, 139, 267-284.*
Chen et al. Physiol. Rev. 2014, 94, 1-34.*
Perez-Miller et al. Nature Structural & Molecular Biology 2010, 17 (2), 159-165.*
Mason et al. BMJ, doi:10.1136/bmj.38042.506748.EE, published Mar. 19, 2004.*
Trevisani et al. PNAS 2007, 104 (33), 13519-13524.*

* cited by examiner

*Primary Examiner* — Sreeni Padmanabhan
*Assistant Examiner* — Irina Neagu
(74) *Attorney, Agent, or Firm* — Pamela J. Sherwood; Bozicevic, Field & Francis LLP

(57) ABSTRACT

Methods and compositions are provided for treating pain in an individual. Aspects of the methods include administering to the individual an agent that promotes ALDH activity. These methods find many uses, for example in treating and preventing nociceptive pain, inflammatory pain, and neuropathic pain.

9 Claims, 11 Drawing Sheets

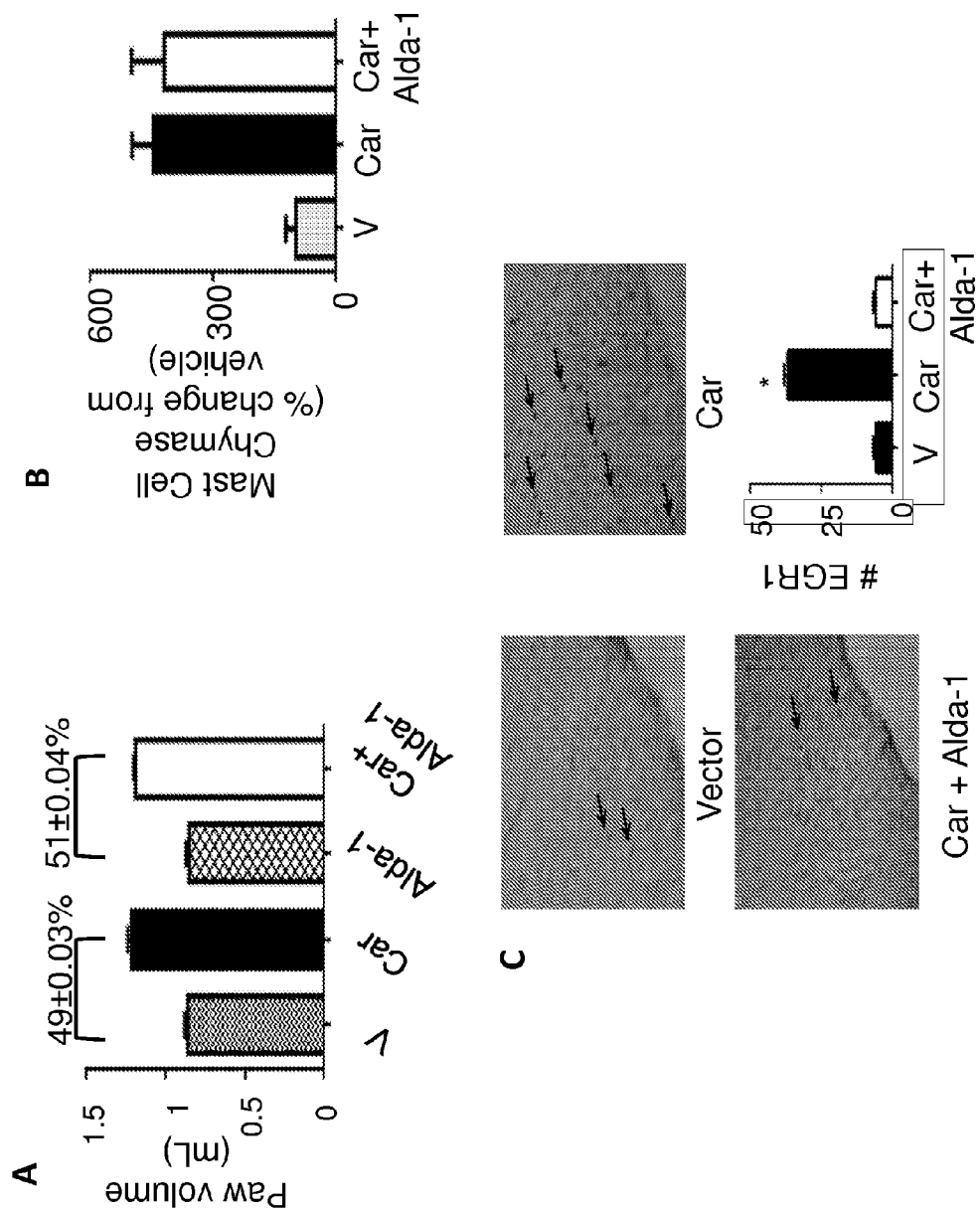
Figure 2A-C

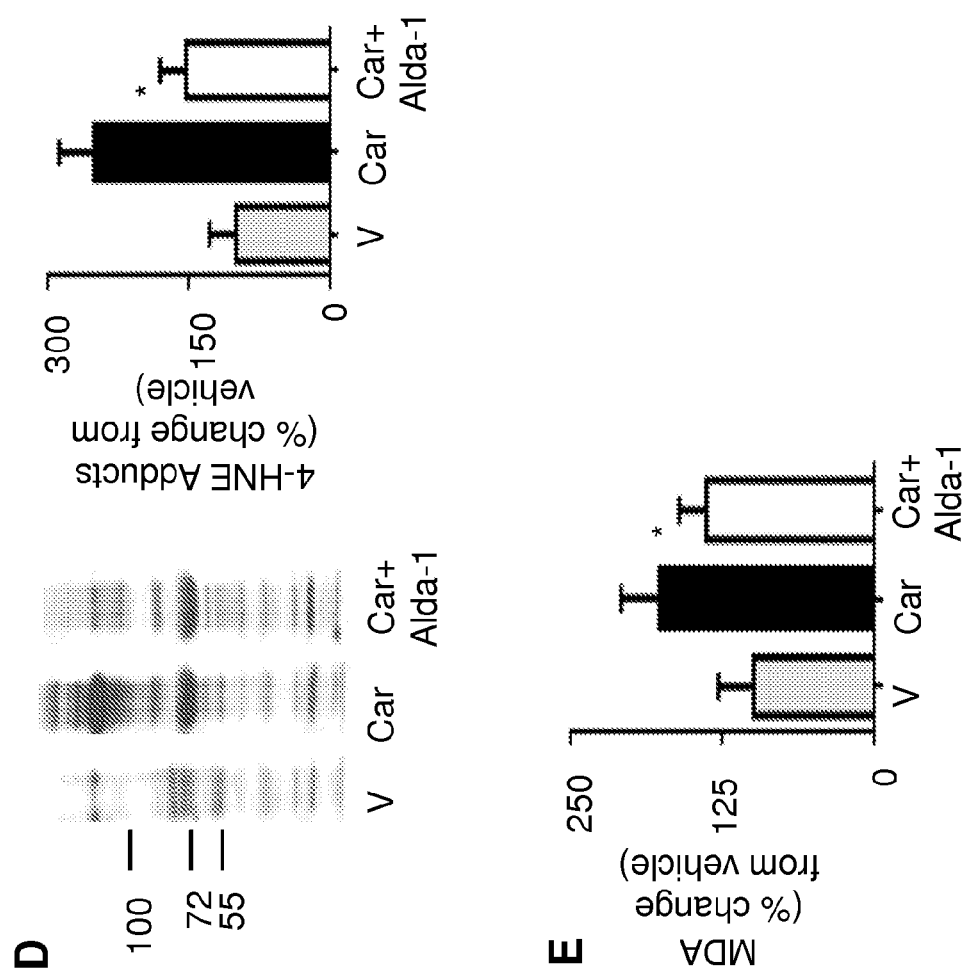
Figure 2D-E

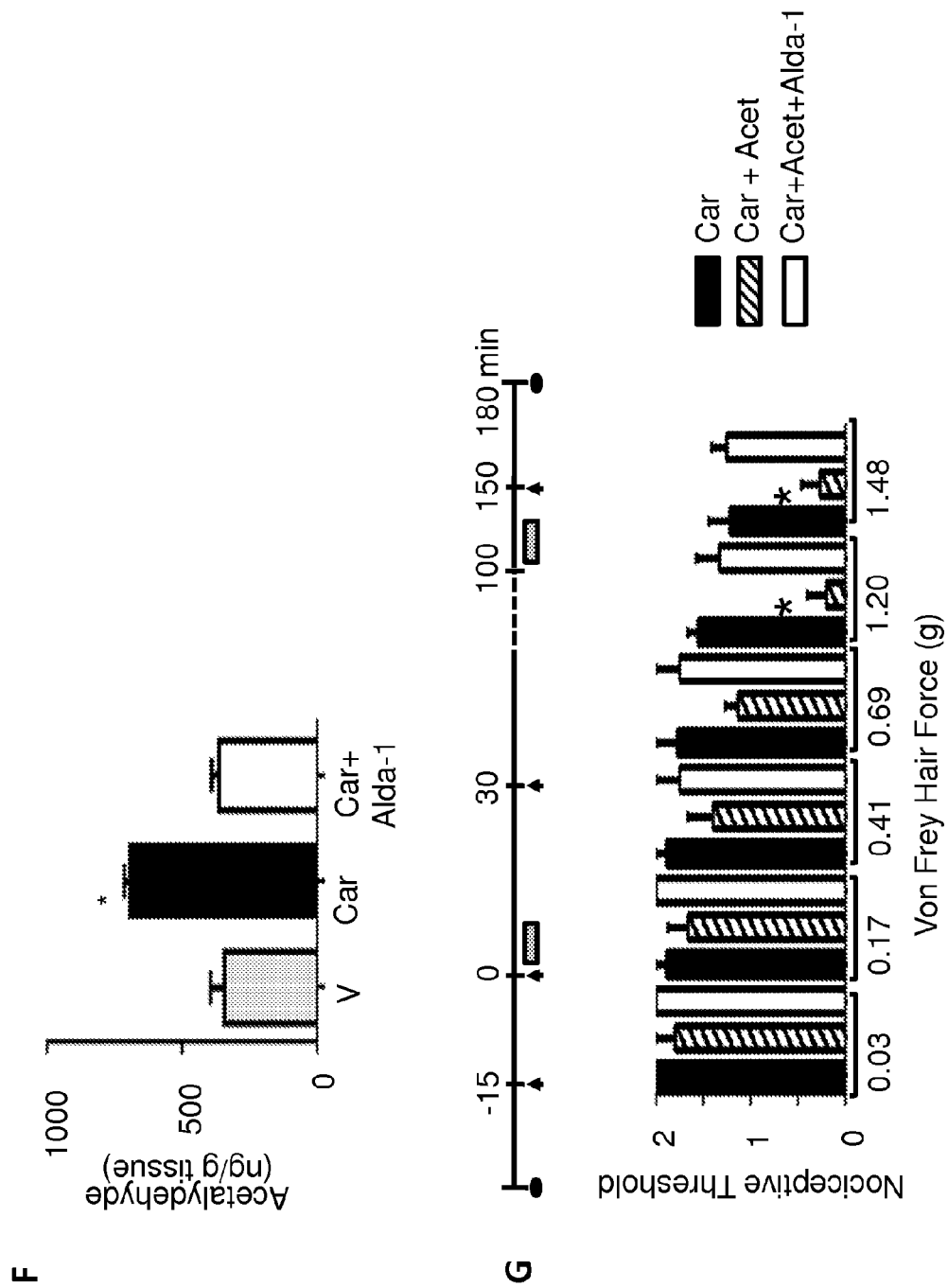
Figure 2F-G

METHODS AND COMPOSITIONS FOR TREATING PAIN

CROSS REFERENCE TO RELATED APPLICATIONS

This application is a National Stage entry of International Application No. PCT/US2013/056432, filed on 23 Aug. 2013, which claims priority from U.S. Provisional Patent Application Ser. No. 61/693,188 filed Aug. 24, 2012; the full disclosure of which is herein incorporated by reference in their entirety.

GOVERNMENT RIGHTS

This invention was made with Government support under contract AA011147 awarded by the National Institute of Health. The Government has certain rights in this invention.

FIELD OF THE INVENTION

This invention pertains to methods and compositions for treating pain.

BACKGROUND OF THE INVENTION

Pain, as defined by the International Association for the Study of Pain, is "An unpleasant sensory and emotional experience associated with actual or potential tissue damage, or described in terms of such damage." (Bonica J J. Pain. 1979; 6(3):247-8). Pain, be it acute or chronic, can be highly debilitating. Current treatments are not wholly effective, and may produce unwanted side effects. As such, effective management of pain requires novel therapeutics suitable for use in individuals. The present invention addresses these issues.

SUMMARY OF THE INVENTION

Methods and compositions are provided for treating pain in an individual. Aspects of the methods include administering to the individual an agent that promotes ALDH activity. These methods find many uses, for example in treating and preventing nociceptive pain, inflammatory pain, and neuropathic pain.

BRIEF DESCRIPTION OF THE DRAWINGS

FIG. 2 demonstrates how ALDH2 activation by Alda-1 reduces aldehydic load and decreases a marker of hyperalgesia at the spinal cord. For A-F, rats were subjected to the protocol described in FIG. 1A and all analyses were carried out 3 hours after carrageenan-induced insult. A. Paw diameter 3 hr after carrageenan injection showed no differences in Alda-1-treated as compared with vehicle-treated rats. B. The levels of mast cell chymase in the paw after carrageenan injection also showed no differences between Alda-1 and vehicle-treated rats. C. Histological slices stained for EGR1, a marker of hyperalgesia in the L4-L6 regions of the spinal cord. EGR1 expression significantly increased in carrageenan-treated animals as compared with naïve rats, and Alda-1 treatment brought EGR1 levels to those seen in baseline (n=6/group, *P<0.01). D. Representative Western blots and quantitation of same for 4-hydroxynonenal (4-HNE) protein adducts in vehicle (V), carrageenan (Car), and carrageenan+Alda-1 (Car+Alda-1) treated groups. Carrageenan significantly increased 4-HNE protein-adducts, as compared with vehicle-treated rats, and 4-HNE adduct protein levels was reduced by Alda-1 treatment (n=5-6/group, *P<0.01). E. Malondialdehyde (MDA) levels assessed as percent change relative to naïve rats. Carrageenan significantly increased MDA levels as compared with naïve rats, which was reduced by Alda-1 treatment (n=6/group, *P<0.05). F. Quantification of acetaldehyde levels in carrageenan-induced inflamed paw. Carrageenan-induced acetaldehyde levels were significantly reduced in Alda-1-treated rats, as compared with those treated with carrageenan alone (n=3/group, *P<0.05). G. Experimental protocol and mouse nociceptive studies with heterozygous ALDH2*2 mice exposed to acetaldehyde when given Alda-1 or vehicle (red arrows) in the presence of carrageenan (50 µg, black arrow), with some mice exposed to acetaldehyde (grey bars). For the ALDH2*2 mice, acetaldehyde exacerbated the pain response, which was rescued by Alda-1 treatment when compared to carrageenan alone, (*P<0.05).

This is the first report of a mitochondrial enzyme regulating nociception and identifies ALDH2 as a potential new target for analgesic drug development.

Figure 5:
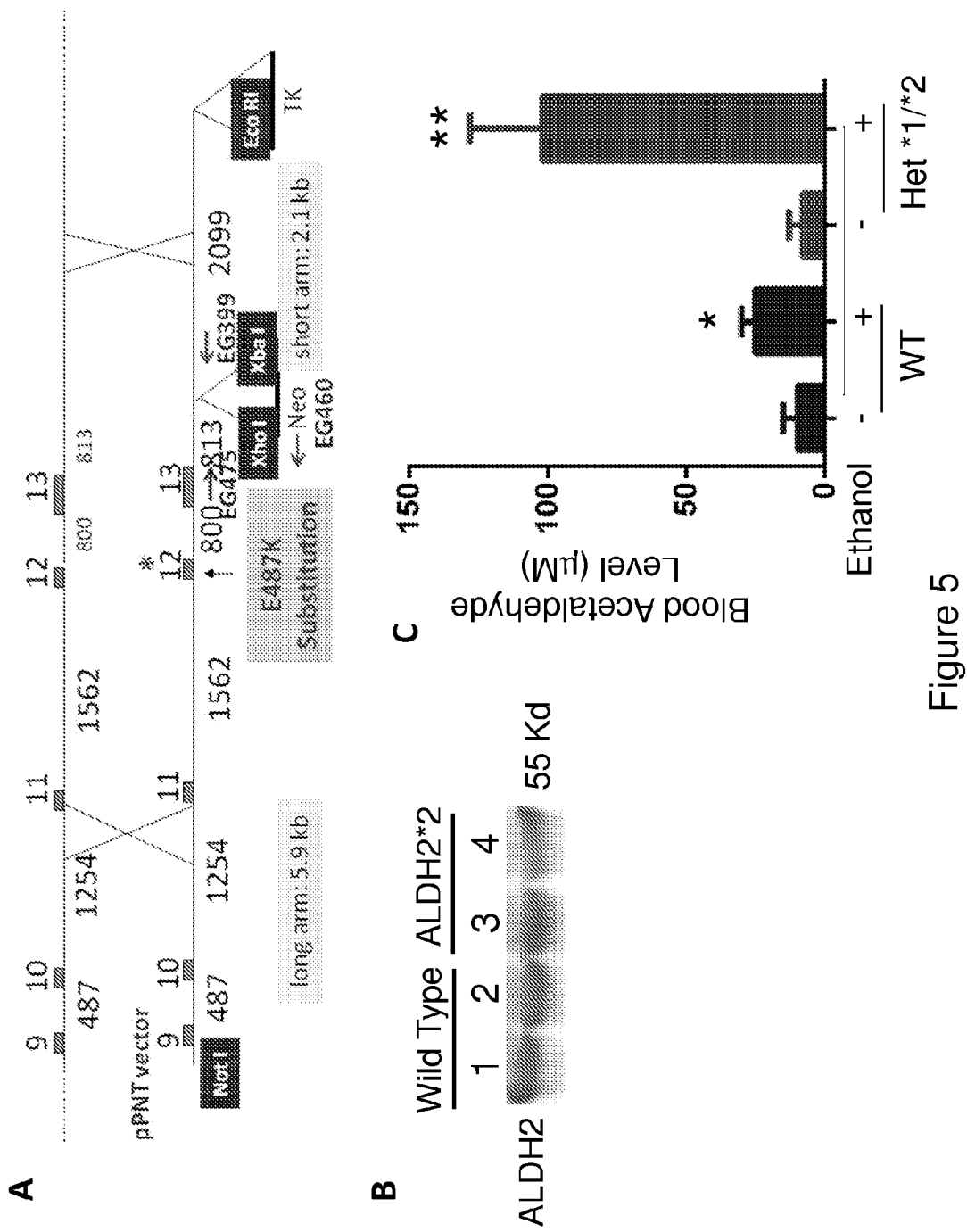

FIG. 5 depicts the generation of the ALDH2*2 mutant mouse. (A) Schematic of the genetically engineered knock-in mutant mice comprise the ALDH2*2 mutation. EG475, EG399 and EG460 are PCR primers used for the knock-in confirmation of the E487K substitution. (B) Western blot for ALDH2. Comparable amounts of ALDH2 and ALDH2*2 protein are generated from the wild type and mutated ALDH2 locus, respectively. (C) Analysis of blood acetaldehyde levels in wild type versus ALDH2*2 mice following administration of ethanol (4 g/kg). Significantly increased levels of acetaldehyde are found in the blood of ALDH2*2 mutant mice, demonstrating that aldehyde dehydrogenase activity in the ALDH2*2 mouse is severely reduced.

Figure 6:
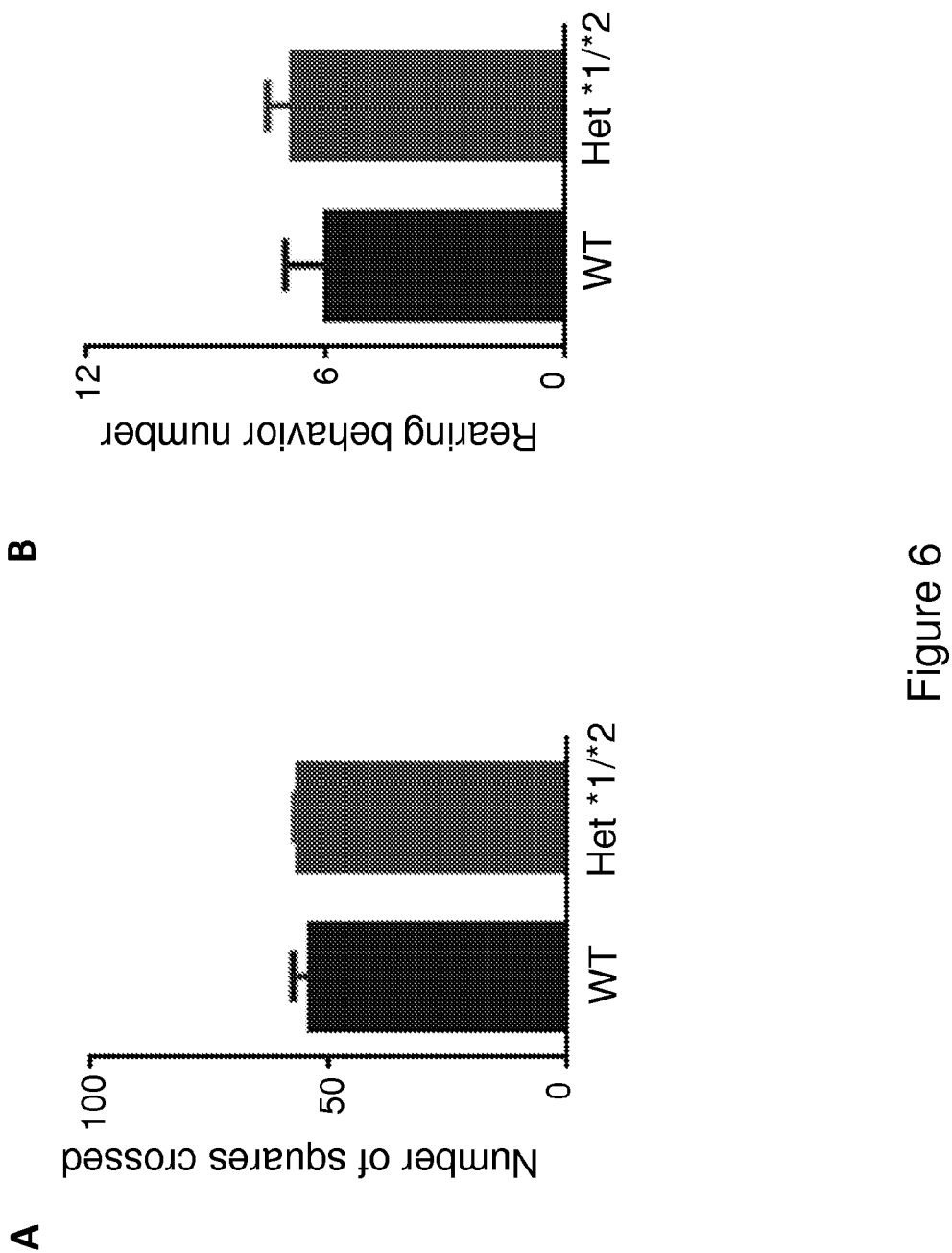

FIG. 6 depicts the behavioral response of wild type ALDH2 (blue bars) and heterozygous ALDH2*1/*2 mice (red bars). A. Mean number of squares crossed in an open field test and B. Number of rearings (Mean±SEM, n=6-7/group).

Figure 7:
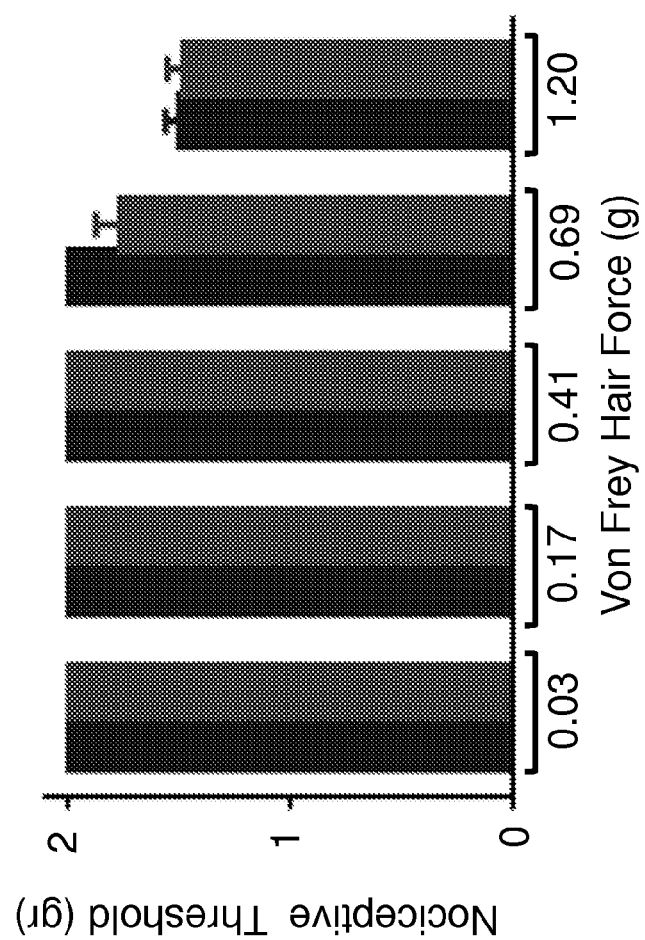

FIG. 7 illustrates the baseline threshold in mice for von Frey hairs (0.03, 0.17, 0.41, 0.69 and 1.20 grams, for both wild type ALDH2 (blue bars) and heterozygous ALDH2*1/*2 mice (red bars) (n=6-7/group; *$P<0.001$).

Figure 8:
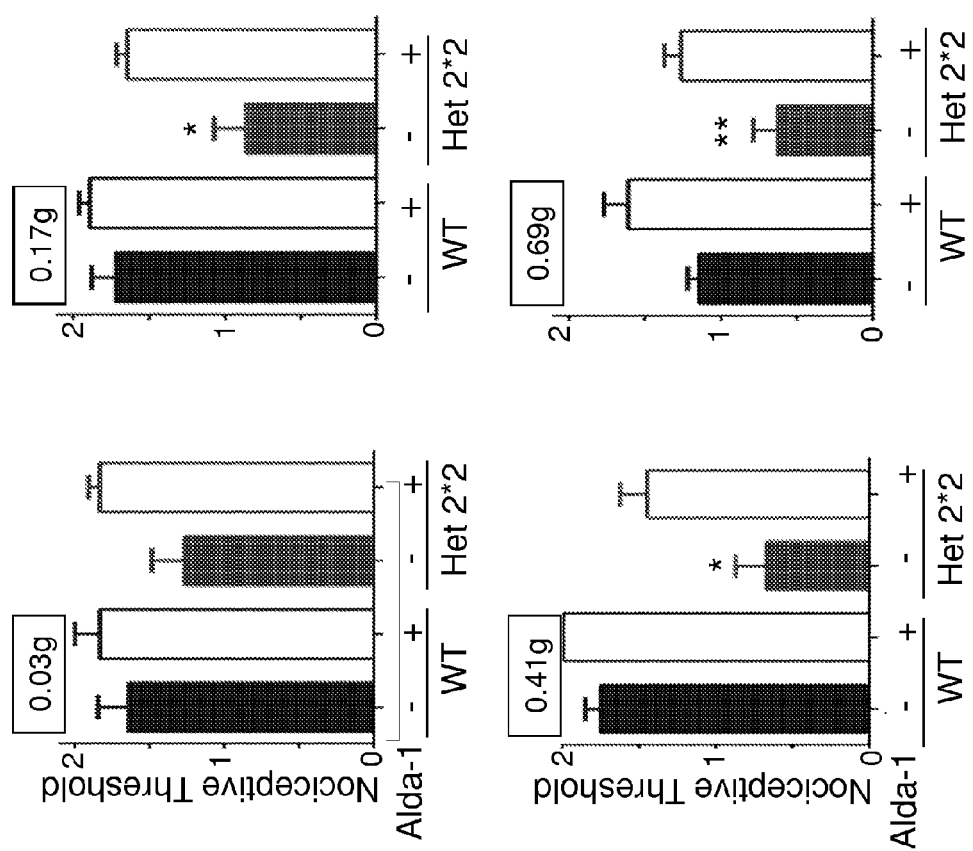

FIG. 8 illustrates the effect of Alda-1 on pain tolerance for von Frey hairs (0.03, 0.17, 0.41 and 0.69 grams, denoted by the number in box at the top left corner of each graph) for both wild type ALDH2 (blue bars) and heterozygous ALDH2*1/*2 mice (red bars). Alda-1 was administered at 3 time points; see the scheme describing the protocol in FIG. 1A. Blue and red solid bars were redrawn from FIG. 1D for comparison (n=6-7/group; *$P<0.001$).

DETAILED DESCRIPTION OF THE INVENTION

Methods and compositions are provided for treating pain in an individual. Aspects of the methods include administering to the individual an agent that promotes ALDH activity. These methods find many uses, for example in treating and preventing nociceptive pain, inflammatory pain, and neuropathic pain. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and compositions are provided for treating pain in an individual. By "pain" or "algesia" it is meant the perception of any aversive or unpleasant sensation that originates from a specific region of the body. By "treatment", "treating" and the like it is generally meant obtaining a desired pharmacologic and/or physiologic effect, i.e. treatment of pain. The terms "individual," "subject," "host," and "patient," are used interchangeably herein and refer to any mammalian subject for whom diagnosis, treatment, or therapy is desired, e.g. murine, rodent, canine, feline, equine, bovine, ovine, primate, human, etc., particularly human. The effect may be prophylactic in terms of completely or partially preventing pain or a symptom thereof and/or may be therapeutic in terms of a partial or complete relief from pain and/or adverse effects attributable to pain. "Treatment" as used herein covers any treatment of pain in a mammal, and includes: (a) preventing pain from occurring in a subject which may be predisposed to pain but has not yet begun to feel it; (b) inhibiting pain, i.e., arresting its development; or (c) relieving pain, i.e., causing regression of, or relief from, pain. The therapeutic agent may be administered before, during or after the onset of pain, e.g. before, during or after the onset of the pain-inducing condition or injury. The treatment of ongoing pain, where the treatment stabilizes or reduces the pain of the patient, is of particular interest. Such treatment is desirably performed prior to complete loss of function in the affected tissues.

There are several different types of pain that are recognized in the art. These include, for example, nociceptive pain, inflammatory pain, and neuropathic pain. By "nociceptive pain" it is meant pain due to signaling in the central nervous system that is evoked by the activation of nerve endings of specialized sensory nerves by noxious stimuli. These sensory nerves, called "nociceptors" or "pain receptors", have nerve cell bodies (soma) that reside in the dorsal root ganglia adjacent to the spinal cord and nerve endings (termini) that are found in the skin and on internal surfaces such as the periosteum or joint surfaces. Examples of nociceptive pain include pain from thermal stimuli, i.e. noxious heat or cold at various temperatures; pain from mechanical stimuli, e.g., excess pressure or mechanical deformation, incisions that break the skin surface; and pain from chemical stimuli, e.g., spices commonly used in cooking (e.g. capsaicin), environmental irritants (e.g. acrolein, mustard oil, allicin), etc. Nociceptors have a certain threshold; that is, they require a minimum intensity of stimulation before they trigger an action potential. Once this threshold is reached, a signal is passed from the nerve ending along the axon into the spinal cord. However, production of prostaglandins (e.g. PGE2) and toxic aldehydes (e.g. 4-Hydroxy-2-nonenal (4-HNE)) by injured cells, e.g. following insult or injury to tissue, e.g. by noxious stimuli as described above, has been shown to lower the pain threshold, inducing hyperalgesia. By "hyperalgesia" it is mean a decrease in the threshold required to trigger an action potential in a nociceptor, i.e. the nociceptor is sensitized such that a low intensity stimulus initiates a painful sensation. In other words, the sensation of pain in response to a stimulus is enhanced. By "inflammatory pain" it is meant pain due to nociceptor stimulation by immune cells during an inflammatory response. Upon insult or injury to tissue (e.g. mechanical, thermal, chemical insult/injury, injury associated with neuropathy, etc.), the cells of the tissue may release factors, e.g. prostaglandins (e.g. PGE2), chemokines, etc. that promote the migration, adhesion and extravasation of leukocytes from the blood to the site of insult/injury. Recruited leukocytes in turn secrete inflammatory mediators, e.g. IL-1 β, LIF, IL-6, Bradykinin, histamine, PGE2, 2-AG, 5-HT, etc., and reactive oxygen species, some of which stimulate nociceptor terminals while promoting the propagation and maturation of the inflammatory response. Thus, inflammatory pain is typically accompanied by inflammation and swelling, e.g. edema, at the site of pain. In some instances, the inflammation may produce hyperalgesia. Hyperalgesia may occur at the site of tissue damage (primary hyperalgesia) and/or in the surrounding undamaged areas (secondary hyperalgesia).

By "neuropathic pain" it is meant pain due to damage to nerves of the peripheral or central nervous system. Common qualities of neuropathic pain include burning or coldness, "pins and needles" sensations, numbness, itching and paroxysmal (electric shock-like) pain. The pain can be acute or chronic, focal or diffuse. Neuropathies are typically caused by diseases of or trauma to nerve(s), or the side-effects of systemic illness or treatment thereof on nerve(s). For example, central neuropathic pain may develop from, e.g., spinal cord injury, multiple sclerosis, or stroke. Peripheral neuropathic pain may arise from, e.g. genetic disease, e.g. Friedreich's ataxia, Charcot-Marie-Tooth disease, Hereditary neuropathy with liability to pressure palsy; metabolic/endocrine conditions, e.g. diabetes; virus, e.g. herpes zoster infection (shingles); HIV-related neuropathies; immune mediated disorders, e.g. Guillain-Barré syndrome, systemic lupus erythematosis, leprosy, Multiple Sclerosis, Sjögren's syndrome, Lyme Disease, sarcoidosis; and nutritional deficiencies, e.g. vitamin deficiencies, toxins, malignancies, etc. Neuropathic pain is common in cancer as a direct result of cancer, e.g. malignancy, on peripheral nerves (e.g., compression by a tumor), or as a side effect of the medical treatment, e.g. chemotherapy, radiation injury or surgery. Damaged nerves may release factors, e.g. prostaglandins (e.g. PGE2), chemokines, etc. that promote nociceptive pain and inflammatory pain as described above. Inflammation may induce hyperalgesia and the development of central sensitization, i.e. sensitization of the central nervous system. In some instances, allodynia is produced. By "allodynia" it is meant pain due to a stimulus which does not normally provoke pain, e.g. pain produced by a mechanical sensation.

Nonlimiting examples of pain that may be treated by the subject methods include nociceptive pain, inflammatory pain, and neuropathic pain. The pain may be cutaneous pain, somatic pain, or visceral pain. The pain may be acute pain, i.e. pain that arises as an awareness of noxious signaling from recently damaged tissue, sometimes complicated by sensitization in the periphery and/or within the CNS. Alternatively, the pain may be chronic pain, i.e. pain without apparent biological value that has persisted beyond the normal tissue healing time (usually taken to be three months).

In some aspects of the subject methods, pain is treated by providing an agent that promotes, i.e. enhances or augments, aldehyde dehydrogenase activity in the individual. In other words, an agent that promotes aldehyde dehydrogenase activity is an analgesic. By "aldehyde dehydrogenase activity" it is meant the activity of enzymes that oxidize (dehydrogenate) aliphatic and aromatic aldehydes to carboxylic acids in an NAD+- or NADP+-dependent reaction. In some aspects, pain may be treated by providing an agent that promotes, i.e. enhances or augments, the activity of an aldehyde dehydrogenase (ALDH), i.e. an ALDH agonist. By an "aldehyde dehydrogenase", or "ALDH", it is meant an enzyme that belongs to the well-known family of enzymes with pyridine-nucleotide-dependent oxidoreductase activity. ALDHs catalyze the oxidation (dehydrogenation) of a wide spectrum of aliphatic and aromatic aldehydic substrates (e.g., a xenogenic aldehyde, a biogenic aldehyde, or an aldehyde produced from a compound that is ingested, inhaled, or absorbed) to carboxylic acids in an $NAD^+$- or $NADP^+$-dependent reaction. For example, ALDH oxidizes aldehydes and acetaldehydes derived from the breakdown of compounds, e.g., toxic compounds that are ingested, that are absorbed, that are inhaled, or that are produced as a result of oxidative stress or normal metabolism, e.g., the metabolism of alcohol to acetaldehyde by alcohol dehydrogenase (ADH), the metabolism of retinol to retinal, etc. An aldehyde dehydrogenase can also exhibit esterase activity, i.e. the hydrolysis of esters, and/or reductase activity, e.g. the metabolism of glyceryl trinitrate (GTN) to 1,2-GDN and inorganic nitrite, which results in the formation of NO. ALDHs are isozymes. By isozymes it is meant enzymes that differ in amino acid sequence but catalyze the same chemical reaction. In other words, the enzymes are encoded by different genes, but process or catalyze the same reaction. These enzymes usually display different kinetic parameters (e.g. different KM values), or different regulatory properties.

ALDHs may be found in the cytosol, the mitochondria, microsome, and other cellular compartment. Examples of aldehyde dehydrogenases include members of the ALDH1 family, including ALDH1A1 (also known as ALDH1, ALDH-E1, ALDH11, and retinal dehydrogenase 1; see GenBank Accession No. NM_000689); ALDH1A2 (also known as RALDH2 or retinal dehydrogenase 2; see GenBank Accession Nos. NM_003888 (isoform 1), NM_170696.2 (isoform 2), NM_170696.2 (isoform 3), and NM_001206897 (isoform 4)); ALDH1A3 (also known as ALDH6, ALDH1A6, RALDH3, or retinal dehydrogenase 3; see Genbank Accession No. NM_000693); ALDH1 B1 (also known as ALDH5 or ALDHX, see GenBank Accession No. NM_000692); ALDH1 L1 (also known as FDH, FTHFD, or cytosolic 10-formyltetrahydrofolate dehydrogenase; see GenBank Accession Nos. NM_001270364 (isoform 1), NM_012190 (isoform 2), and NM_001270365 (isoform 3)); ALDH1L2 (also known as mtFDH or mitochondrial 10-formyltetrahydrofolate dehydrogenase, see GenBank Accession No. NM_001034173); members of the ALDH2 family, in particular ALDH2 (see GenBank Accession Nos. NM_000690 (isoform 1) and NM_001204889 (isoform 2); members of the ALDH3 family, e.g. ALDH3A1 (also known as ALDH3; see GenBank Accession Nos. NM_001135168.1 (variant 1), NM_000691.4 (variant 2), and NM_001135167.1 (variant 3)); ALDH3A2 (also known as ALDH10, FALDH, or fatty aldehyde dehydrogenase; see GenBank Accession Nos. NM_001031806.1 (isoform 1) and NM_000382.2 (isoform 2)); ALDH3B1 (also known as ALDH4; ALDH7; see GenBank Accession Nos. NM_000694.2 (isoform a) and NM_001030010.1 (isoform b)); ALDH3B2 (also known as ALDH8; see GenBank Accession Nos. NM_000695.3 (variant 1) and NM_001031615.1 (variant 2)); members of the ALDH4 family, particularly ALDH4A1 (also known as ALDH4; P5CD; GenBank Accession Nos. NM_003748.3 (isoform a) and NM_001161504.1 (isoform b)); members of the ALDH5 family, particularly ALDH5A1 (also known as SSDH, or succinate-semialdehyde dehydrogenase, mitochondrial; see GenBank Accession Nos. NM_170740.1 (isoform 1) and NM_001080.3 (isoform 2)); members of the ALDH6 family, particularly ALDH6A1 (also known as MMSDH or methylmalonate-semialdehyde dehydrogenase [acylating], mitochondrial; see GenBank Accession No. NM_005589.2); members of the ALDH7 family, particularly ALDH7A1 (see GenBank Accession Nos. NM_001182.4 (isoform 1), NM_001201377 (isoform 2), and NM_001202404 (isoform 3)); members of the ALDH8 family, particularly ALDH8A1 (also known as ALDH12; see GenBank Accession Nos. NM_022568.3 (isoform 1), NM_170771.2 (isoform 2) and NM_001193480.1 (isoform 3); members of the ALDH9 family, particularly ALDH9A1 (also known as E3, ALDH4, ALDH7, ALDH9, TMABADH or 4-trimethylaminobutyraldehyde dehydrogenase; see GenBank Accession No. NM_000696.3); members of the ALDH16 family, particularly ALDH16A1 (see GenBank Accession Nos. NM_153329.3 (isoform 1) and NM_001145396.1 (isoform 2); and members of the ALDH18 family, particularly ALDH18A1 (GSAS, P5CS, PYCS, ARCL3A, or delta-1-pyrroline-5-carboxylate synthase; see GenBank Accession Nos. NM_002860.3 (isoform 1) and NM_001017423.1 (isoform 2)). An ALDH polypeptide can exhibit one or more of the following enzymatic activities: a) a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid); b) an esterase activity; and c) a reductase activity. More information regarding the members of the ALDH family of proteins may be found on the world wide web by typing in "www" followed by "aldh.org".

The term "ALDH" is used herein to encompass any known native ALDH polypeptide or variant thereof. By "native polypeptide" it is meant a polypeptide found in nature. For example, native ALDH polypeptides include any human ALDH as described herein, the sequences for which may be found at the GenBank Accession Numbers described herein, as well as ALDH homologs that naturally occur in humans and ALDH orthologs that naturally occur in other eukaryotes, e.g. in mice, rodents, canines, cats, equines, bovines, primates. By "variant" it is meant a mutant of the native polypeptide having less than 100% sequence identity with the native sequence. For example, a variant may be a polypeptide having 60% sequence identity or more with a full length native ALDH, e.g. 65%, 70%, 75%, or 80% or more identity, such as 85%, 90%, or 95% or more identity, for example, 98% or 99% identity with the full length native ALDH. Variants also include fragments of a native ALDH polypeptide that have aldehyde dehydrogenase activity, e.g. a fragment comprising residues 18-517 of ALDH2 or the comparable sequence in an ALDH homolog or ortholog. Variants also include polypeptides that have aldehyde dehydrogenase activity and 60% sequence identity or more with a fragment of a native ALDH polypeptide, e.g. 65%, 70%, 75%, or 80% or more identity, such as 85%, 90%, or 95% or more sequence identity, for example, 98% or 99% identity with the comparable fragment of the native ALDH polypeptide.

Human ALDHs are provided here as examples of native ALDH polypeptides, but it will be appreciated by the ordinarily skilled artisan that native ALDH polypeptides from any eukaryote and variants thereof may be employed in the treatment of pain, these native ALDH polypeptides being readily identified using publicly available resources such as PubMed or NCBI Blast. The aldehyde dehydrogenase activity of these ALDH polypeptides in mitotic cells can be readily confirmed by any convenient method for detecting the oxidation of aldehydes to carboxylic acids in an $NAD^+$-dependent or an $NADP^+$-dependent reaction., e.g. as known in the art or as described herein. The term "ALDH polypeptide" encompasses a polypeptide having a length of from about 400 amino acids to about 600 amino acids (aa), e.g., from about 400 aa to about 450 aa, from about 450 aa to about 500 aa, from about 500 aa to about 550 aa, or from about 550 aa to about 600 aa.

In some embodiments, an agent that promotes ALDH activity promotes a dehydrogenase activity of ALDH, that is, the agent promotes dehydrogenase activity in oxidizing an aldehyde (e.g., a xenogenic aldehyde, a biogenic aldehyde, or an aldehyde produced from a compound that is ingested, inhaled, or absorbed) to the corresponding acid. In other embodiments, an agent that promotes ALDH activity promotes an esterase activity of ALDH. In other embodiments, an agent that promotes ALDH activity promotes a reductase activity of ALDH. For example, ALDH can convert nitroglycerin to nitric oxide (NO) via its reductase activity.

In some embodiments, a subject ALDH agonist promotes, i.e. enhances or augments, the enzymatic activity of a particular ALDH isozyme. For example, in some embodiments, a subject ALDH agonist promotes, i.e. enhances or augments, the enzymatic activity of the aldehyde dehydrogenase ALDH2. "ALDH2" or "mitochondrial aldehyde dehydrogenase-2" is a mitochondrial matrix homotetramer with broad specificity and a low $K_m$ for acetaldehydes. ALDH2 is a member of the ALDH1B subfamily of ALDHs and is localized to the mitochondrial matrix. Human ALDH2 has a sequence disclosed in GenBank Accession Nos. NM_000690 (isoform 1) and NM_001204889 (isoform 2); a mouse ALDH2 amino acid sequence is found under GenBank Accession No. NP_033786; and a rat ALDH2 amino acid sequence is found under GenBank Accession No. NP_115792. The term "ALDH2" encompasses an aldehyde dehydrogenase that exhibits substrate specificity, e.g., that preferentially oxidizes aliphatic aldehydes. The term "ALDH2" encompasses an enzymatically active polypeptide having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1. The term "ALDH2" as used herein also encompasses fragments, fusion proteins, and variants (e.g., variants having one or more amino acid substitutions, addition, deletions, and/or insertions) that retain ALDH2 enzymatic activity, e.g. 1% or more enzymatic activity, 2% or more enzymatic activity, 5% or more enzymatic activity, 10% or more enzymatic activity, 20% or more enzymatic activity, 30% or more enzymatic activity, 50% or more enzymatic activity, 80% or more enzymatic activity, 90% or more enzymatic activity, or 100% enzymatic activity, i.e. the enzymatic activity of the variant is no different from that of native ALDH2. Enzymatically active ALDH2 variants, fragments, fusion proteins, and the like can be verified by adapting the methods described herein. One example of an ALDH2 variant is ALDH2*2 (SEQ ID NO:2), wherein a lysine residue replaces a glutamate in the active site at position 487 of processed human ALDH2 (residue 504 of unprocessed ALDH2, SEQ ID NO:1), or at a position in a non-human ALDH2 corresponding to amino acid 487 of human ALDH2. This mutation is referred to as the "E487K mutation"; the "E487K variant"; or the "Glu504Lys polymorphism". See, e.g., Larson et al. (2005) J. Biol. Chem. 280:30550; and Li et al. (2006) J. Clin. Invest. 116:506. Individuals that are homozygous for ALDH2*2 have almost no ALDH2 activity, and those heterozygous for the mutation have reduced activity.

Any convenient agent that promotes the activity of an ALDH (i.e. any "ALDH agonist"), or more particularly, ALDH2 (i.e. any "ALDH2 agonist"), may be employed as an analgesic, i.e. to treat pain in the subject methods. For example, an ALDH agonist that finds use in the subject methods may increase the amount of ALDH in a cell, or may activate or increase the activity of an ALDH, e.g. by activating an ALDH directly or by promoting the activity of proteins upstream of ALDH, etc. So, for example, when it is desirable to treat pain by administering an agent that promotes the activity of ALDH2, the subject methods will encompass agents that increase the amount of ALDH2 in a cell, or that activate or increase the activity of ALDH2 or a variant thereof, e.g. by activating ALDH2 or variant thereof directly or by promoting the activity of proteins upstream of ALDH2, etc.

For example, agents that are small molecule compounds find use in the subject methods. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992). Small molecule compounds can be provided directly to the medium in which the cells are being cultured, for example as a solution in DMSO or other solvent.

As another example, agents that would be suitable for use in the subject methods include nucleic acids, for example, nucleic acids that encode ALDH polypeptides or active fragments thereof. Many vectors useful for transferring nucleic acids into target cells are available. The vector may be maintained episomally, e.g. as plasmid, minicircle DNA, virus-derived vector such as cytomegalovirus, adenovirus, etc., or it may be integrated into the target cell genome, through homologous recombination or random integration, e.g. retrovirus derived vectors such as MMLV, HIV-1, ALV, etc. The nucleic acid agent may be provided directly to the cells. In other words, the cells are contacted with vectors comprising the nucleic acid of interest such that the vectors are taken up by the cells. Methods for contacting cells with nucleic acid vectors, such as electroporation, calcium chloride transfection, and lipofection, are well known in the art. Alternatively, the nucleic acid agent may be provided to cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject cells are targeted by the packaged viral particles. Methods of introducing the retroviral vectors comprising the nucleic acid ALDH agonist into packaging cell lines and of collecting the viral particles that are generated by the packaging lines are well known in the art.

Vectors used for providing nucleic acid of interest to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by 5 fold or more, by 10 fold or more, by at least about 100 fold or more, more usually by at least about 1000 fold. In addition, vectors used for providing nucleic acid to the subject cells may include genes that must later be removed, e.g. using a recombinase system such as Cre/Lox, or the cells that express them destroyed, e.g. by including genes that allow selective toxicity such as herpesvirus TK, bcl-xs, etc Agents suitable for promoting ALDH activity in the present invention also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. Polypeptides may be fused to a polypeptide permeant domain to promote the transport of the polypeptide agent across the cell membrane and into the cell. A number of permeant domains are known in the art and may be used in the polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include polyarginine motifs, for example, the region of amino acids 34-56 of HIV-1 rev protein, nona-arginine, octa-arginine, and the like. (See, for example, Futaki et al. (2003) Curr Protein Pept Sci. 2003 Apr; 4(2): 87-96; and Wender et al. (2000) Proc. Natl. Acad. Sci. U.S.A 2000 Nov. 21; 97(24): 13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The polypeptide agent for use in the subject methods may be produced from eukaryotic produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

For example, when it is desirable to promote the activity of ALDH2, any convenient agent that promotes the enzymatic activity of ALDH2 may be employed. One example of such an agent is a functional ALDH polypeptide or functional fragment or variant thereof, e.g. an ALDH2 polypeptide, a functional polypeptide or fragment thereof of the isozyme ALDH1, etc. Specific enzymatically active ALDH2 polypeptide variants, fragments, fusion proteins, and the like can be verified by adapting the methods described herein. Another example is a small molecule allosteric activator of ALDH2, e.g. Alda-1 (N-(1,3-benzodioxol-5-ylmethyl)-2,6-dichlorobenzamide) or an analog thereof, e.g.the water soluble derivative Alda-44. Other examples of ALDH2 agonists include those disclosed in US applications US20090082431, US20100063100, US 20100113423, and U.S. Pat. No. 7,560,241, the full disclosures of which are herein incorporated by reference.

Whether a compound is an ALDH agonist can be readily ascertained. Assays for dehydrogenase activity of ALDH are known in the art, and any known assay can be used. Examples of dehydrogenase assays are found in various publications, including, e.g., Sheikh et al. ((1997) J. Biol. Chem. 272:18817-18822); Vallari and Pietruszko (1984) J. Biol. Chem. 259:4922; and Farres et al. ((1994) J. Biol. Chem. 269:13854-13860).

As an example of an assay for dehydrogenase activity, ALDH aldehyde dehydrogenase activity is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes NAD+ (e.g., 0.8 mM NAD+, or higher, e.g., 1 mM, 2 mM, or 5 mM NAD+) and an aldehyde substrate such as 14 μM propionaldehyde. Reduction of NAD+ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide (NAD+) to its reduced form, NADH, at 340 nm, as described in US 2005/0171043; and WO 2005/057213. In an exemplary assay, the reaction is carried out at 25° C. in 0.1 sodium pyrophosphate (NaPPi) buffer, pH 9.0, 2.4 mM NAD+ and 10 mM acetaldehyde as the substrate. Enzymatic activity is measured by a reductive reaction of NAD+ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043 and WO 2005/057213. Detection of fluorescent resorufin at 590 nm provides amplified and more sensitive signals for any change in ALDH aldehyde dehydrogenase enzymatic activity. NADP+ can be used in place of NAD+ in this assay. Suitable substrates include, but are not limited to, octylaldehyde, phenylacetaldehyde, retinaldehyde, and 4-hydroxynonenal. Any ALDH polypeptides (e.g., ALDH1, ALDH2, ALDH3, ALDH5, etc.) can be used. The enzyme used in the assay can be purified (e.g., at least about 75% pure, at least about 80% pure, at least about 85% pure, at least about 90% pure, at least about 95% pure, at least about 98% pure, or at least about 99% pure). Recombinant ALDH enzyme can also be used in the assay.

As another example, the effect of a compound on aldehyde dehydrogenase activity of an ALDH polypeptide can be assayed as described in Wierzchowski et al. ((1996) Analytica Chimica Acta 319:209), in which a fluorogenic synthetic substrate, e.g., 7-methoxy-1-naphthaldehyde is used. For example, the reaction could include 7-methoxy-1-naphthaldehyde, NAD+, an ALDH polypeptide, and an ALDH agonist to be tested; fluorescence (excitation, 330 nm; emission 390 nm) is measured as a readout of enzymatic activity.

Whether a compound increases an esterase activity of ALDH can be determined using any known assay for esterase activity. For example, esterase activity of ALDH2 can be determined by monitoring the rate of p-nitrophenol formation at 400 nm in 25 mM N,N-Bis (2-hydroxyethyl)-2-amino ethanesulfonic acid (BES) (pH 7.5) with 800 μM p-nitrophenyl acetate as the substrate at room temperature in the absence or presence of added NAD+. A pH-dependent molar extinction coefficient of 16 mM-1 cm-1 at 400 nm for nitrophenol can be used. See, e.g., Larson et al. (2007) J. Biol. Chem. 282:12940). Esterase activity of ALDH can be determined by measuring the rate of p-nitrophenol formation at 400 nm in 50 mM Pipes (pH 7.4) with 1 mM p-nitrophenylacetate as the substrate. A molar extinction coefficient of 18.3×103 M-1 cm-1 at 400 nm for p-nitrophenolate can be used for calculating its rate of formation. See, e.g., Ho et al.(2005) Biochemistry 44:8022).

Whether a compound increases a reductase activity of ALDH can be determined using any known assay for reductase activity. A reductase activity of ALDH can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence ALDH2. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 ml in ethanol for subsequent TLC separation and scintillation counting. See, e.g., Zhang and Stamler (2002) Proc. Natl. Acad. Sci. USA 99:8306.

In some embodiments, a subject ALDH agonist is specific for (e.g., selective for) ALDH2, e.g., a subject ALDH2 agonist increases an enzymatic activity of an ALDH2 enzyme, but does not substantially increase the same enzymatic activity of cytosolic aldehyde dehydrogenase-1 (ALDH1), e.g., a subject ALDH2 agonist increases an enzymatic activity of an ALDH1 enzyme, if at all, by less than about 15%, less than about 10%, less than about 5%, less than about 2%, or less than about 1%, when used at a concentration that increases the same enzymatic activity of an ALDH2 enzyme by at least about 5% or more. In some embodiments, a subject ALDH2 agonist does not substantially increase the enzymatic activity of alcohol dehydrogenase (ADH), e.g., a subject ALDH2 agonist increases the enzymatic activity of an ADH, if at all, by less than about 5%, less than about 2%, or less than about 1%, when used at a concentration that increases the enzymatic activity of an ALDH2 enzyme by at least about 5% or more.

For example, in some embodiments, a subject ALDH2 agonist is specific for (e.g., selective for) ALDH2, e.g., a subject ALDH2 agonist increases dehydrogenase activity of an ALDH2 enzyme, but does not substantially increase the dehydrogenase activity of cytosolic aldehyde dehydrogenase-1 (ALDH1), e.g., a subject ALDH2 agonist increases dehydrogenase activity of an ALDH1 enzyme, if at all, by less than about 15%, less than about 10%, less than about 5%, less than about 2%, or less than about 1%, when used at a concentration that increases dehydrogenase activity of an ALDH2 enzyme by at least about 5% or more. In some embodiments, a subject ALDH2 agonist does not substantially increase dehydrogenase activity of alcohol dehydrogenase (ADH), e.g., a subject ALDH2 agonist increases the dehydrogenase activity of an ADH, if at all, by less than about 5%, less than about 2%, or less than about 1%, when used at a concentration that increases the dehydrogenase activity of an ALDH2 enzyme by at least about 5% or more.

In some embodiments, a subject ALDH agonist increases an enzymatic activity of certain ALDH enzymes, e.g. the isozymes ALDH1 and ALDH2, but does not substantially increase the same enzymatic activity of any other ALDH enzyme, e.g., a subject ALDH agonist increases an enzymatic activity of an ALDH isozyme other than ALDH1 and ALDH2 by 15% or less, by 10% or less, by 5% or less, by 2% or less, by 1% less, e.g. by a negligible amount, if at all, when used at a concentration that increases the same enzymatic activity of an ALDH1 and ALDH2 enzyme by at least about 15% or more.

The agent that promotes ALDH activity (the "ALDH agonist") is typically provided to cells in a therapeutically effective amount. By a "therapeutically effective amount" or "efficacious amount" it is meant an amount of an agent that, when administered to a mammal or other subject for treating pain, is sufficient, either alone in one or more doses, or in combination in one or more doses with another agent, to prevent such pain or to effect such relief for the pain, i.e. to reduce the pain, to achieve analgesia for the pain. The "therapeutically effective amount" will vary depending on the compound, the cause of the pain and its severity and the age, weight, etc., of the subject to be treated.

For example, a therapeutically effective amount or effective dose of an ALDH agonist is the dose that, when administered for a suitable period of time, usually at least 5 minutes or more, e.g. 15 minutes or more, 1 hour or more, 2 hours or more, or 3 hours or more, in some instances 4 hours or more, 5 hours or more, or 6 hours or more, sometimes 12 hours or more or 24 hours or more, will evidence an alteration in the responsiveness of an individual to a noxious stimulus that elicits pain. For example, a therapeutically effective amount or effective dose of an ALDH agonist (or ALDH2 agonist) is the dose that, when administered for a suitable period of time, usually at least about 5 minutes or more, e.g. 15 minutes or more, one hour or more, 2 hours or more, or 3 hours or more, in some instances 4 hours or more, 5 hours or more, or 6 hours or more, sometimes 12 hours or more or 24 hours or more, will increase the pain threshold by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, or at least about 10-fold. In some instances, the ALDH agonist may be prophylactically therapeutic, e.g. the therapeutically effective amount will be the amount sufficient to prevent pain, for example when delivered prior to the condition that would result in pain, or after the onset of the condition that would result in pain but prior to the onset of pain. In some instances, the ALDH agonist may be administered after the onset of pain, in which case the therapeutically effective amount will be the amount sufficient to reduce the sensation of pain by at least about 5%, at least about 10%, at least about 15%, or at least about 20%, in some cases by at least about 25%, at least about 30%, at least about 35%, at least about 40%, at least about 45%, at least about 50%, or at least about 60%, more usually at least about 70%, at least about 80%, at least about 90% or at least about 98% (i.e. to negligible amounts), in some instance by 100%, in other words, rendering the person free of pain. It will be understood by those of skill in the art that this effect may be achieved by a single dose or by multiple doses.

The therapeutically effective dose may be readily determined using any convenient preclinical or clinical assay e.g. as known in the art or described herein. For example, in a preclinical setting, pain threshold may be assessed in an animal administered an ALDH agonist using a paw pressure test or von Frey test. Such results are typically compared to the results from a control, or reference, sample, e.g. an animal not administered the ALDH agonist. In a clinical setting, pain may be measured on a quantitative or a qualitative scale. Any convenient method may be used to measure pain in such instances. For example, pain may be measured on the visual analogue scale (VAS), the numerical rating scale (NRS), the verbal descriptor scale (VDS). Methods particularly useful in children and the infirm include the FLACC (i.e. face, Legs, Activity, Cry, and Consolability) Behavior Pain Scale, the Touch Visual Pai (TVP) Scale, the Wong-Baker FACES Pain Rating Scale, and the Pain Thermometer. See, e.g., "Guide to Pain Management in Low-Resourse Settings", A. Kopf and N.B. Patel, eds., IASP, Seattle, © 2010. In some embodiments, the method further comprises measuring the pain felt by the individual and determining that the pain has been reduced following treatment with the agent as compared to before administration of the agent.

Biochemically speaking, an therapeutically effective amount or effective dose of an ALDH agonist will be the amount required to increase the enzymatic activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH polypeptide in the absence of the agonist. In certain embodiments, the ALDH polypeptide is an ALDH2 polypeptide or variant thereof.

In some embodiments, an effective amount of a subject ALDH agonist is the amount effective to increase a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH polypeptide in the absence of the agonist. In certain embodiments, the ALDH polypeptide is an ALDH2 polypeptide or variant thereof.

In some embodiments, an effective amount of a subject ALDH agonist is the amount effective to increase the esterase activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH polypeptide in the absence of the agonist. In certain embodiments, the ALDH polypeptide is an ALDH2 polypeptide or variant thereof.

In some embodiments, an effective amount of a subject ALDH agonist is the amount effective to increase the reductase activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH polypeptide in the absence of the agonist. In certain embodiments, the ALDH polypeptide is an ALDH2 polypeptide or variant thereof.

The extent to which ALDH enzymatic activity is modulated by an ALDH agonist can be readily determined by any convenient way known to one of ordinary skill in the art of molecular biology or neurobiology or as described herein. For example, ALDH enzymatic activity may be determined spectrophotometrically by monitoring the reductive reaction of NAD+ to NADH at A340 nm in the presence of acetaldehyde. As another example, the presence and concentration of aldehyde adducts, e.g. 4-Hydroxinonenal (4-HNE) protein adducts, in tissue may be assessed by Western blotting using an antibody specific for HNE amino acid adducts (Calbiochem, NJ) In this way, the agonistic effect of the agent may be confirmed.

Calculating the effective amount or effective dose of ALDH agonist to be administered is within the skill of one of ordinary skill in the art, and will be routine to those persons skilled in the art. Needless to say, the final amount to be administered will be dependent upon a variety of factors, include the route of administration, the nature of the disorder or condition that is to be treated, and factors that will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally or topically administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

An ALDH agonist may be administered to an individual by any of a number of well-known methods in the art or described herein for the administration of small molecules, peptides, and nucleic acids to a subject. The ALDH agonist can be incorporated into a variety of formulations. More particularly, the ALDH agonist of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the ALDH agonist can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including caveoil-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

The calculation of the effective amount or effective dose of ALDH agonist to be administered is within the skill of one of ordinary skill in the art, and will be routine to those persons skilled in the art. Needless to say, the final amount to be administered will be dependent upon the route of administration, upon the nature of the pain that is to be treated, the health and physical condition of the individual to be treated, age, the taxonomic group of individual to be treated (e.g., human, non-human primate, primate, etc.), the degree of resolution desired, the formulation of the ALDH agonist composition, the treating clinician's assessment of the medical situation, and other relevant factors. It is expected that the amount will fall in a relatively broad range that can be determined through routine trials. For example, the amount of ALDH agonist employed to treat pain is not more than about the amount that could otherwise be irreversibly toxic to the subject (i.e., maximum tolerated dose). In other cases the amount is around or even well below the toxic threshold, but still in an effective concentration range, or even as low as threshold dose.

Individual doses are typically not less than an amount required to produce a measurable effect on the individual, and may be determined based on the pharmacokinetics and pharmacology for absorption, distribution, metabolism, and excretion ("ADME") of the ALDH agonist or of its by-products, and thus based on the disposition of the composition within the subject. This includes consideration of the route of administration as well as dosage amount, which can be adjusted for topical (applied directly where action is desired for mainly a local effect), enteral (applied via digestive tract for systemic effects, or local effects when retained in part of the digestive tract), or parenteral (applied by routes other than the digestive tract for systemic or local effects) applications. For instance, administration of the ALDH agonist may be via injection, e.g. intravenous, intramuscular, intracranial, or intraventricular injection, or a combination thereof.

The ALDH agonist may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g, by infusion) can be repeated over a desired period, e.g., repeated over a period of about 6 hours, about 12 hours, about 24 hours, or about 48 hours to about once every several days, for example, about every five days, etc. It also can be administered prior, at the time of, or after other therapeutic interventions, e.g. the administration of other analgesics, the administration of therapeutics directed at the cause of the pain, surgical intervention, etc. The ALDH agonist can also be administered as part of a combination therapy, in which at least one of an immunotherapy, a diabetes therapy, a cancer therapy, etc. also is administered to the subject.

Disposition of the ALDH agonist and its corresponding biological activity within a subject is typically gauged against the fraction of ALDH agonist present at a target of interest. Thus dosing regimens in which the ALDH agonist is administered so as to accumulate in a target of interest over time can be part of a strategy to allow for lower individual doses. This can also mean that, for example, the doses of ALDH agonist that are cleared more slowly in vivo can be lowered relative to the effective concentration calculated from in vitro assays (e.g., effective amount in vitro approximates mM concentration, versus less than mM concentrations in vivo).

As an example, the effective amount of an ALDH agonist can be gauged from the $EC_{50}$ of a given ALDH agonist concentration. By "$EC_{50}$" is intended the plasma concentration required for obtaining 50% of a maximum effect in vivo. In related embodiments, dosage may also be determined based on $ED_{50}$ (effective dosage).

In general, with respect to the subject methods, an effective amount of ALDH agonist is usually not more than 100× the calculated $EC_{50}$. For instance, the amount of a ALDH agonist that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated $EC_{50}$. The effective amount may be about 1× to 30× of the calculated $EC_{50}$, and sometimes about 1× to 20×, or about 1× to 10× of the calculated $EC_{50}$. The effective amount may also be the same as the calculated $EC_{50}$ or more than the calculated $EC_{50}$. The $EC_{50}$ can be calculated by modulating the enzymatic activity of the ALDH polypeptide, e.g.

the aldehyde dehydrogenase activity, in vitro. The procedure can be carry out by methods known in the art or as described in the examples below.

Effective amounts of dose and/or dose regimen can readily be determined empirically from assays, from safety and escalation and dose range trials, individual clinician-patient relationships, as well as in vitro and in vivo assays such as those described herein and illustrated in the Experimental section, below. For example, if a concentration used for carrying out the subject method in mice ranges from about 1 mg/kg to about 25 mg/kg based on the body weight of the mice, an example of a concentration of the ALDH agonist that can be employed in human may range about 0.083 mg/kg to about 2.08 mg/kg. Other dosage may be determined from experiments with animal models using methods known in the art (Reagan-Shaw et al. (2007) *The FASEB Journal* 22:659-661).

The ALDH agonist can be incorporated into a variety of formulations. More particularly, the ALDH agonist may be formulated into pharmaceutical compositions by combination with appropriate pharmaceutically acceptable carriers or diluents.

Pharmaceutical preparations are compositions that include one or more ALDH agonists present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the ALDH agonist can be achieved in various ways, including transdermal, intradermal, oral, buccal, rectal, parenteral, intraperitoneal, intradermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For inclusion in a medicament, the ALDH agonist may be obtained from a suitable commercial source. As a general proposition, the total pharmaceutically effective amount of the ALDH agonist administered parenterally per dose will be in a range that can be measured by a dose response curve.

ALDH agonist-based therapies, i.e. preparations of ALDH agonist to be used for therapeutic administration, may be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The ALDH agonist-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection. Alternatively, the ALDH agonist may be formulated into lotions for topical administration.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatment of pain. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapies that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

In some embodiments, the agent that promotes ALDH activity may be administered alone, e.g. in the absence of other therapeutic agents. In other embodiments, the ALDH agonist may be administered in combination with other agents, e.g. other analgesics, e.g. NSAIDS, COX-2 inhibitors, etc., or may be administered in conjunction with other therapies, e.g. surgical interventions.

Utility

The subject methods find many uses for treating pain in an individual. For example, the subject methods find use in treating nociceptive pain. Towards this end, it is shown in the working examples herein that the administration of an ALDH agonist reduces the sensitivity to pain and hyperalgesia induced by PGE2, and by binding directly to nociceptors, reduces the levels of aldehydes that have been shown by others to promote pain (Trevisani et al. 4-Hydroxynonenal, an endogenous aldehyde, causes pain and neurogenic inflammation through activation of the irritant receptor TRPA1. Proc. Natl. Acad. Sci. 2007 104(33):13519-24). In some embodiments, the nociceptive pain is acute nociceptive pain. In some embodiments, the nociceptive pain is chronic nociceptive pain. In some embodiments, the agent is administered prior to the onset of nociceptive pain. For example, the agent may be administered prior to insult/injury to tissue, e.g. 5 minutes or more, 15 minutes or more, 30 minutes or more, 45 minutes or more, 1 hour or more, 2 hours or more, 3 hours or more, 4 hours or more, 5 hour or more, or 6 hours or more, and typically not more than 6 hours before the anticipated insult/injury to tissue, e.g. as a prophylactic, e.g., to prevent pain following insult/injury to the tissue. In other embodiments, the agent is administered after the onset of pain, e.g. 5 minutes or more, 10 minutes or more, 15 minutes or more, 20 minutes or more, 30 minutes or more, 45 minutes or more, 1 hour or more, 2 hours or more, 3 hours or more, 4 hours or more, 5 hours or more, 6 hours or more, 12 hours or more, or 24 hours or more after the onset of pain. For example, the agent may be administered after the insult/injury to tissue, but before the development of inflammation. Additionally or alternatively, the agent may be administered after the insult/injury to tissue and after the development of inflammation.

The subject methods also find use in treating inflammatory pain. Towards this end, it is shown in the working examples herein that the administration of an ALDH agonist reduces the sensitivity to pain and hyperalgesia induced by carrageenan in a well-characterized animal model for inflammatory pain. In some embodiments, the inflammatory pain is acute inflammatory pain. In some embodiments, the inflammatory pain is chronic inflammatory pain. In either instance, the pain will typically be accompanied by inflammation and edema. In some embodiments, the agent is administered prior to the onset of inflammatory pain. For example, the agent may be administered prior to insult/injury to tissue, e.g. 5 minutes or more, 15 minutes or more, 30 minutes or more, 45 minutes or more, 1 hour or more, 2 hours or more, 3 hours or more, 4 hours or more, 5 hour or more, or 6 hours or more, and typically not more than 6 hours before the anticipated insult/injury to tissue, e.g. as a prophylactic, i.e. to prevent inflammatory pain following insult/injury to the tissue. As another example, the agent may be administered after the insult/injury to tissue, but before the development of inflammation. Additionally or alternatively, the agent may be administered after the development of inflammation and pain, e.g. 5 minutes or more, 10 minutes or more, 15 minutes or more, 20 minutes or more, 30 minutes or more, 45 minutes or more, 1 hour or more, 2 hours or more, 3 hours or more, 4 hours or more, 5 hours or more, 6 hours or more, 12 hours or more, or 24 hours or more after the onset of pain.

The subject methods may also be applied to the treatment of neuropathic pain. For example, as mentioned above, it is shown herein that the administration of an ALDH agonist reduces the sensitivity to pain and hyperalgesia induced by PGE2. It is well known in the art that PGE2 is involved in the pathogenesis of neuropathic pain. See, e.g., Ma W, Eisenach J C. Four PGE2 EP receptors are up-regulated in injured nerve following partial sciatic nerve ligation. Exp Neurol. 2003 Oct; 183(2):581-92; Mabuchi, T et al. Membrane-associated prostaglandin E synthase-1 is required for neuropathic pain. NeuroReport 15(9):1395-1398; Wang, C. et al. Prostaglandin E2 potentiation of P2X3 receptor mediated currents in dorsal root ganglion neurons. Molecular Pain 2007 2:22. In some embodiments, the agent is administered to an individual with a disease in the absence of any neuropathic pain, e.g. as a prophylactic, e.g. to prevent neuropathic pain during disease. In other embodiments, the agent is administered after the onset of neuropathic pain. Examples of neuropathic pain that may be treated by the subject methods include pain associated with mononeuropathy, with mononeuritis multiplex, with polyneuropathy, with autonomic neuropathy, or with neuritis. Diseases exhibiting symptoms of neuropathy that may be treated using the subject methods include genetic diseases (e.g. Friedreich's ataxia, Charcot-Marie-Tooth disease, Hereditary neuropathy with liability to pressure palsy); metabolic/endocrine diseases (e.g. diabetes mellitus, chronic renal failure, porphyria, amyloidosis, liver failure, hypothyroidism); immune-mediated disease or disorder (e.g. Guillain-Barré syndrome, systemic lupus erythematosis, leprosy, Multiple Sclerosis, Sjögren's syndrome, Lyme Disease, sarcoidosis); and malignancies. Other conditions include neuropathy due to drugs (e.g. vincristine, metronidazole, phenytoin, nitrofurantoin, isoniazid, ethyl alcohol, statins, fluoroquinolone), organic metals, heavy metals, excess intake of vitamin B6 (pyridoxine); vitamin deficiency states (e.g. vitamin B12 (cyanocobalamin), vitamin A, vitamin E, vitamin B1 (thiamin)), physical trauma (e.g. compression, pinching, cutting, projectile injuries (i.e. gunshot wound)); strokes including prolonged occlusion of blood flow, electric discharge, including lightning strikes; virus (shingles, HIV), and medical treatment (e.g. radiation, chemotherapy, surgery).

In some embodiments, the subject methods find use in treating pain promoted by prostaglandin E2 (PGE2), i.e. PGE2-mediated pain. By "prostagladin E2" or "PGE2" it is meant the cyclooxygenase metabolite of arachidonic acid that, when released from damaged cells, neurons, or leukocytes, stimulates nociceptor signaling. In certain embodiments, the PGE2-mediated pain is PGE2-mediated nociceptive pain. In certain embodiments, the PGE2-mediated pain is PGE2-mediated inflammatory pain. In certain embodiments, the PGE2-mediated pain is PGE2-mediated neuropathic pain. Elevated levels of PGE2, e.g. in blood/plasma, in a tissue biopsy, etc., may be measured using any convenient method, for example, ELISA (e.g. Biotrak™ PGE2 enzyme immunoassay kit, PGE2 ELISA kits by Enzo Life Sciences).

In some embodiments, the subject methods find use in treating pain promoted by aldehydes, e.g. acetaldehyde, 4-hydroxy-2-nonenal (4-HNE), etc. i.e. aldehyde-mediated pain. In certain embodiments, the aldehyde-mediated pain is aldehyde-mediated nociceptive pain. In certain embodiments, the aldehyde-mediated pain is aldehyde-mediated inflammatory pain. In certain embodiments, the aldehyde-mediated pain is aldehyde-mediated neuropathic pain. Elevated levels of aldehydes, e.g., 4-HNE, or protein adducts thereof, e.g. HNE adducts, e.g. in blood/plasma, in a tissue biopsy, etc., may be measured using any convenient method, for example, GC-MS (Spies-Martin et al. J. Chromatogr B Analyt Technol Biomed Life Sci 2002. 774(2): 231-9), ELISA (e.g. OxiSelect™ HNE Adduct ELISA kit), labeling with a fluorescent probe such as 2-aminopyridine (2-AP) (Wakiti et al. Free Radic Biol Med 2011. 51(1):1-4), etc.

In some instances, the subject methods may be used to treat a human for pain. In some embodiments, a human to be treated according to a subject method is one that has two "wild-type" or "native" ALDH2 alleles, e.g., the ALDH2 encoded by the two wild-type ALDH2 alleles has a glutamic acid at position 487. In other embodiments, a human to be treated according to a subject method is one that has one or two hypomorphic alleles. By a "hypomorphic allele" it is meant that the allele encodes a variant of the protein with reduced activity relative to the level of activity of the wild type. One example of a hypomorphic allele is the "ALDH2*2" allele, i.e. the ALDH2 allele that encodes a polypeptide comprising a lysine as amino acid position 487 of SEQ ID NO:2. In some embodiments, the ALDH2 encoded by one or both ALDH2 alleles comprises a lysine as amino acid position 487. The E487K polymorphism is a semidominant polymorphism, and results in an ALDH2 tetramer that has significantly lower enzymatic activity than "wild-type" ALDH2. Thus, individuals who are heterozygous or homozygous for the ALDH2*2 allele have much lower in vivo ALDH2 activity levels than individuals who are homozygous for the "wild-type" ALDH2 allele. Individuals who are heterozygous or homozygous for the ALDH2*2 allele are expected to benefit from treatment with a subject ALDH2 agonist, because the level of ALDH2 activity in such individuals is particularly low, and any increase of ALDH2 activity levels would be expected to provide a therapeutic effect.

Individuals having an ALDH2 hypomorphic allele may be identified by any convenient method in the art for detecting such mutations. For example, where a subject is genotyped for an ALDH2 single nucleotide polymorphism (SNP), e.g. the ALDH2*2 polymorphism, a subject or patient sample, e.g., cells or collections thereof, e.g., tissues, is assayed to determine the nucleotide sequence of the gene at that polyporphism, or the amino acid sequence encoded by the gene at that polymorphism, e.g., by using one or more genotyping reagents, such as but not limited to nucleic acid reagents, including primers, etc., which may or may not be labeled, as described below, amplification enzymes, buffers, etc. In practicing the subject methods, the sample obtained from the subject is assayed to determine the genotype of the subject from which the sample was obtained with respect to at least one, i.e., one or more, polymorphisms, where polymorphisms of interest are referred to herein as target polymorphisms, examples of which are mentioned above. Any convenient protocol for assaying a sample for the above one or more target polymorphisms may be employed in the subject methods. In certain embodiments, the target polymorphism will be detected at the protein level, e.g., by assaying for a polymorphic protein. In yet other embodiments, the target polymorphism will be detected at the nucleic acid level, e.g., by assaying for the presence of nucleic acid polymorphism, e.g., an single nucleotide polymorphism (SNP) that cause expression of the polymorphic protein.

For example, polynucleotide samples derived from (e.g., obtained from) an individual may be employed. Any biological sample that comprises a polynucleotide from the individual is suitable for use in the methods of the invention. The biological sample may be processed so as to isolate the polynucleotide. Alternatively, whole cells or other biological samples may be used without isolation of the polynucleotides contained therein. Detection of a target polymorphism in a polynucleotide sample derived from an individual can be accomplished by any means known in the art, including, but not limited to, amplification of a sequence with specific primers; determination of the nucleotide sequence of the polynucleotide sample; hybridization analysis; single strand conformational polymorphism analysis; denaturing gradient gel electrophoresis; mismatch cleavage detection; and the like. Detection of a target polymorphism can also be accomplished by detecting an alteration in the level of a mRNA transcript of the gene; aberrant modification of the corresponding gene, e.g., an aberrant methylation pattern; the presence of a non-wild-type splicing pattern of the corresponding mRNA; an alteration in the level of the corresponding polypeptide; and/or an alteration in corresponding polypeptide activity.

Detection of a target polymorphism by analyzing a polynucleotide sample can be conducted in a number of ways. A test nucleic acid sample can be amplified with primers which amplify a region known to comprise the target polymorphism(s). Genomic DNA or mRNA can be used directly. Alternatively, the region of interest can be cloned into a suitable vector and grown in sufficient quantity for analysis. The nucleic acid may be amplified by conventional techniques, such as a polymerase chain reaction (PCR), to provide sufficient amounts for analysis. The use of the polymerase chain reaction is described in a variety of publications, including, e.g., "PCR Protocols (Methods in Molecular Biology)" (2000) J. M. S. Bartlett and D. Stirling, eds, Humana Press; and "PCR Applications: Protocols for Functional Genomics" (1999) Innis, Gelfand, and Sninsky, eds., Academic Press. Once the region comprising a target polymorphism has been amplified, the target polymorphism can be detected in the PCR product by nucleotide sequencing, by SSCP analysis, or any other method known in the art. In performing SSCP analysis, the PCR product may be digested with a restriction endonuclease that recognizes a sequence within the PCR product generated by using as a template a reference sequence, but does not recognize a corresponding PCR product generated by using as a template a variant sequence by virtue of the fact that the variant sequence no longer contains a recognition site for the restriction endonuclease.

PCR may also be used to determine whether a polymorphism is present by using a primer that is specific for the polymorphism. Such methods may comprise the steps of collecting from an individual a biological sample comprising the individual's genetic material as template, optionally isolating template nucleic acid (genomic DNA, mRNA, or both) from the biological sample, contacting the template nucleic acid sample with one or more primers that specifically hybridize with a target polymorphic nucleic acid molecule under conditions such that hybridization and amplification of the template nucleic acid molecules in the sample occurs, and detecting the presence, absence, and/or relative amount of an amplification product and comparing the length to a control sample. Observation of an amplification product of the expected size is an indication that the target polymorphism contained within the target polymorphic primer is present in the test nucleic acid sample. Parameters such as hybridization conditions, polymorphic primer length, and position of the polymorphism within the polymorphic primer may be chosen such that hybridization will not occur unless a polymorphism present in the primer(s) is also present in the sample nucleic acid. Those of ordinary skill in the art are well aware of how to select and vary such parameters. See, e.g., Saiki et al. (1986) Nature 324:163; and Saiki et al (1989) Proc. Natl. Acad. Sci. USA 86:6230.

Alternatively, various methods are known in the art that utilize oligonucleotide ligation as a means of detecting polymorphisms. See, e.g., Riley et al. (1990) Nucleic Acids Res. 18:2887-2890; and Delahunty et al. (1996) Am. J. Hum. Genet. 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6 carboxyfluorescein (6 FAM), 2',7' dimethoxy 4',5' dichloro 6 carboxyfluorescein (JOE), 6 carboxy X rhodamine (ROX), 6 carboxy 2',4',7',4,7 hexachlorofluorescein (HEX), 5 carboxyfluorescein (5 FAM) or N,N,N',N' tetramethyl 6 carboxyrhodamine (TAMRA), radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid may be sequenced using any convenient sequencing protocol, such as a dideoxy chain termination method protocol. Genomic DNA or mRNA may be used directly. If mRNA is used, a cDNA copy may first be made. If desired, the sample nucleic acid can be amplified using a PCR. A variety of sequencing reactions known in the art can be used to directly sequence the relevant gene, or a portion thereof in which a specific polymorphism is known to occur, and detect polymorphisms by comparing the sequence of the sample nucleic acid with a reference polynucleotide that contains a target polymorphism. Any of a variety of automated sequencing procedures can be used. See, e.g., WO 94/16101; Cohen et al. (1996) Adv. Chromatography 36:127-162.

Hybridization with the variant sequence may also be used to determine the presence of a target polymorphism. Hybridization analysis can be carried out in a number of different ways, including, but not limited to Southern blots, Northern blots, dot blots, microarrays, etc. The hybridization pattern of a control and variant sequence to an array of oligonucleotide probes immobilized on a solid support, as described in U.S. Pat. No. 5,445,934, or in WO 95/35505, may also be used protocols for detecting the presence of variant sequences. Identification of a polymorphism in a nucleic acid sample can be performed by hybridizing a sample and control nucleic acids to high density arrays containing hundreds or thousands of oligonucleotide probes. See, e.g.

Cronin et al. (1996) Human Mutation 7:244-255; and Kozal et al. (1996) Nature Med. 2:753-759.

Single strand conformational polymorphism (SSCP) analysis; denaturing gradient gel electrophoresis (DGGE); mismatch cleavage detection; and heteroduplex analysis in gel matrices can also be used to detect polymorphisms. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels. The aforementioned techniques are well known in the art. Detailed description of these techniques can be found in a variety of publications, including, e.g., "Laboratory Methods for the Detection of Mutations and Polymorphisms in DNA" (1997) G. R. Taylor, ed., CRC Press, and references cited therein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Pain is an international health problem, affecting approximately 1 in every 5 individuals (Goldberg DS, et al., (2011) Pain as a global public health priority. BMC public health 11: 770). Opioids are a commonly prescribed drug and in the US, over 130 million vicodin prescriptions are written annually (Okie S, (2010) A flood of opioids, a rising tide of deaths. The New England Journal of Medicine 363: 1981-1985). However, the opioid drug class leads to secondary health complications including accidental overdose and death and to opioid addiction, another serious health issue. Anti-inflammatory pain medications, such as cyclooxygenase-2 inhibitors, may also cause gastrointestinal bleeding and increased risk of cardiac events (Mukherjee D, et al., (2001) Risk of cardiovascular events associated with selective COX-2 inhibitors. JAMA: the journal of the American Medical Association 286: 954-959). Thus, discovering other molecular events regulating pain may provide a means to develop additional therapeutics for pain control.

Initial observations suggest that reactive aldehydes, including 4-hydroxynonenal and acetaldehyde, cause pain when directly applied to rodents (Bang S, et al., (2007) Transient receptor potential A1 mediates acetaldehyde-evoked pain sensation. Eur J of Neuro, 26: 2516-2523; Trevisani M, et al., (2007) 4-Hydroxynonenal, an endogenous aldehyde, causes pain and neurogenic inflammation through activation of the irritant receptor TRPA1. Proc Nat Acad Sci USA 104: 13519-13524). However, it is unknown whether altering the enzymatic activity of the mitochondrial aldehyde dehydrogenase-2 (ALDH2), which can catalyze removal of these reactive aldehydes, may alter pain response. Understanding how this enzyme mediates pain is also important since a common inactivating point mutation ALDH2*2 in the mitochondrial aldehyde dehydrogenase 2 (ALDH2; Glu487 to Lys487) occurs in 0.54 billion Han Chinese (Brooks P J, et al., (2009) The alcohol flushing response: an unrecognized risk factor for esophageal cancer from alcohol consumption. PLoS Med 6: e50). The ALDH2*2 mutation causes a flushing response after ethanol consumption. The ALDH2*2 mutation also causes a reduced ability to metabolize other reactive aldehydes, including acetaldehyde and 4-hydroxynonenal (4-HNE). Here, the contribution of ALDH2 enzymatic activity to inflammatory-induced hyperalgesia, and whether a small molecule ALDH2 activator may be a potential drug to reduce pain is determined.

Materials and Methods

General Methods. All procedures were in accordance with the guidelines by the International Association for the Study of Pain and approved by both the Institutional Animal Care and Use Committee at Stanford University (#25505) and the Butantan Institute, Sao Paulo, Brazil (CEUAIB #838). Both mice and rats were used. All behavioral tests were performed between 9:00 am and 4:00 pm by observers that were blinded to the treatment groups. For mice, both C57/BL6 and an ALDH2 *1/*2 heterozygous knock-in mice on C57/BL6 background were used. Male Wistar rats (170-190 grams) and mice (18-21 grams) were housed in a temperature and light-controlled room for at least 3 days before use.

Mice. ALDH2*2 knock-in mice with a C57/BL6 background were generated by homologous recombination (FIG. 5A). The 8.0 kb genomic fragment encompassing the mouse ALDH2 locus was cloned to the gene-targeting vector, pPNT, to introduce a single amino acid substitution. Site-directed mutagenesis introduced a single nucleotide substitution (G to C) within exon 12 of the ALDH2 genomic fragment corresponding to the position of human E487K mutation. Plasmid DNA from the constructed pPNT vector was electroporated to embryonic stem (ES) cells. Positive ES clones were selected based on the neomycin and thymine kinase markers and confirmed by PCR, RFLP and by DNA sequencing. Positive ES cells were microinjected into C57/BL6 blastocytes and implanted into pseudopregnant females.

Germ-line transmission of the ALDH2 E487K mutation by homologous recombination was derived from selected ES cell lines from founder mice. The genotype of the E487K mutation was confirmed by direct genomic DNA sequencing of PCR fragments from amplified genomic DNA. The specific primers

EG475 (TACTGTCAAAGTGCCACAGAAGAACTCG-TAA) (SEQ ID NO:3),

EG460 (AACCTGCGTGCAATCCATCTTGT-TCAATGG) (SEQ ID NO:4) and

EG399 (TTGGCCTTCCACTGGGAGTGGGTC-CCTCTGTC) (SEQ ID NO:5)

were used for the amplification of a 1.3 kb fragment from exon 13 to the 3' untranslated region of neomycin marker and a 3.0 kb fragment from exon 13 to downstream of the neomycin marker, respectively, for presence of the mutated allele. In contrast, for the wild type allele, a 1.4 kb fragment devoid of the neomycin marker was amplified using EG475 and EG399 primers.

The expression of the mutant ALDH2 E487K mutant protein with a charge change as a result of the glutamate to lysine substitution was also confirmed by isoelectric focusing gel electrophoresis and Western blot using an ALDH2-specific antibody (Santa Cruz Biotechnology, 1:500). The founder mice were back crossed to the C57BL/6 background for at least 7 generations to achieve a homogeneous genetic background and the E487K mutation was transmitted as a single Mendelian gene.

Rats. Male Wistar rats (170-190 g) were provided by Charles River Laboratories or Butantan Institute Animal Facility and housed in a temperature-controlled (22±1° C.) and light-controlled (12/12 h light/dark cycle) room. All rats were housed in their surrounding for at least 3 days. Groups of 5-6 rats were used.

Drugs Used. 0.1 ml saline (control), carrageenan (200 µg for rats, 100 µg for mice; Marine Colloids), or prostaglandin E2 (100 ng, Sigma) was administered by intraplantar injection into the right hind paw to induce hyperalgesia. These doses were chosen based on previous studies by our laboratory groups (Aley K O, et al., (2000) Chronic hypersensitivity for inflammatory nociceptor sensitization mediated by the epsilon isozyme of protein kinase C. The Journal of neuroscience: the official journal of the Society for Neuroscience 20: 4680-4685; Konno K, et al., (2008) Crotalphine, a novel potent analgesic peptide from the venom of the South American rattlesnake Crotalus durissus terrificus. Peptides 29: 1293-1304).

Alda-1 dose (2 mg/kg/per injection, dissolved in 50% PEG/50% DMSO) was established in preliminary studies and given in multiple doses due to its estimated short half-life. Alda-1 was injected subcutaneously to the dorsal side of the neck 15 minutes before carrageenan or saline, and again at 30 and 150 minutes after carrageenan, prostaglandin E2 or saline injection. One subset of animals received Alda-1 only 30 and 150 minutes after carrageenan injection. Where indicated, naloxone (1 mg/kg per injection) or vehicle (saline) was given 10 minutes prior to each Alda-1 treatment to the dorsal side of the neck.

Nociception Assessment. The experimental performer was blinded to both genotype and/or treatments. Nociceptive response was assessed by the von Frey method for mice and the Randall-Selitto method for rats immediately before and 180 minutes after carrageenan or prostaglandin E2 injection. Both mice and rats were acclimated to the testing equipment one day before baseline testing.

von Frey hair testing method: Hind paw nociception was assessed with six different von Frey hairs (0.03, 0.17, 0.41, 0.69, 1.20 and 1.48 g). Mice were placed individually in a plastic cage with a wire mesh bottom. After acclimation for at least 15 min, a von Frey hair was pressed perpendicularly against the plantar skin surface and held for approximately 5 seconds until hair slightly buckled. Using the same stimulation intensity as the 0.03 g von Frey hair, each individual hair was applied six times to each hind paw at intervals of several seconds.

Since the response to each von Frey stimulus is fairly subjective, we used a method of objectifying these nociceptive responses by assigning a specific number to the response. Our scoring system consisted of: 2=no response, 1=withdraws paw from hair and 0=immediate flinching or hind paw licking. This method was previously shown by others to provide a reliable, objective assessment of pain response using von Frey hairs (Dale C S, et al., (2009) Analgesic properties of S100A9 C-terminal domain: a mechanism dependent on calcium channel inhibition. Fundamental & clinical pharmacology 23: 427-438; Takasaki I, et al., (2000) Allodynia and hyperalgesia induced by herpes simplex virus type-1 infection in mice. Pain 86: 95-101).

Randall-Selitto method: Nociceptive threshold was determined using the Randall-Selitto paw pressure test (Ugo-Basile), as previously described (Gutierrez V P, et al., (2008) Crotalphine induces potent antinociception in neuropathic pain by acting at peripheral opioid receptors. European journal of pharmacology 594: 84-92). The baseline values varied between 65-75 g of force. Animals with baseline out of this range (about 10%) were excluded prior to initiating the study in order to achieve uniform testing.

Edema Assessment. Inflammation-induced edema of the injected paw was assessed using a plethysmometer (Ugo Basile) (Clapper J R, et al., (2010) Anandamide suppresses pain initiation through a peripheral endocannabinoid mechanism. Nature neuroscience 13: 1265-1270; Van Arman C G, et al., (1965) Some details of the inflammation caused by yeast and carragenin. J Pharmacol Exp Ther 150: 328-333).

Evaluation of general motor activity. Possible changes in ALDH2*2 knock-in mice general activity were investigated in an open-field arena. Hand-operated counters were used to score ambulation (locomotion) frequency (number of floor units entered) and rearing frequency (number of times the animal stood on hind legs). Each animal was individually placed in the centre zone and behavioral parameters were recorded for 3 min (Broadhurst P L, (1960) The place of animal psychology in the development of psychosomatic research. Fortschr Psychosomatic Medicine 1: 63-69; Gutierrez V P, et al., (2008) Crotalphine induces potent antinociception in neuropathic pain by acting at peripheral opioid receptors. European journal of pharmacology 594: 84-92).

Blood Acetaldehyde Determination. Blood samples (50-100 µl) were drawn from the retro-orbital sinus under anesthesia. Levels of acetaldehyde were determined by a fluorescence-based HPLC method, as described previously (Peng GS, et al., (1999) Involvement of acetaldehyde for full protection against alcoholism by homozygosity of the variant allele of mitochondrial aldehyde dehydrogenase gene in Asians. Pharmacogenetics 9: 463-476). See also FIG. 5C.

Tissue Acetaldehyde Measurements. Paw samples were quickly sealed in microcentrifuge tubes, weighed and 3 volumes (v/w) of 0.75 mg/mL Liberase T L (Roche, Indianapolis, Ind.) was added for overnight digestion at 37° C. Acetaldehyde standard solutions (100-5000 ng/mL) and the tissue samples were reacted with saturated 2,4 dinitrophenylhydrazine solution.

To establish LC-MS/MS conditions, the standard of acetaldehyde 2,4-dinitrophenyl-hydrazine (DNPH) was used. Chromatograms of standards were used to establish characteristic retention times of acetaldehyde, and verified the MS signal was linear over the range of 0.1-5 µg/mL. The acetaldehyde peak area derivatives were calculated and plotted against the concentration of the calibration standards using Analyst®1.5.1 software.

Aliquots (30 µL) were taken from each paw homogenate sample. Acetaldehyde in samples of paw homogenate was extracted by adding methanol containing 40 μg/mL DNPH (150 μL). Both unknown samples and standards were vortexed and centrifuged to separate the precipitate. Ten microliters of sample extracts were injected into LC MS/MS for analysis. Automatic peak detection, integration and data processing were performed by the AB SCIEX Analyst 1.5.1 software package. Concentrations of acetaldehyde were calculated by plotting peak area of unknown samples against a standard curve. The data were normalized to the paw volume obtained plesthysmografically.

Acetaldehyde Experiments. ALDH2 *1/*2 mice were subjected to a sub-threshold dose of carrageenan (50 μg) which did not cause hyperalgesia. A subset of these mice was exposed to acetaldehyde vapor with or without Alda-1. Acetaldehyde was delivered by placing the mice in an enclosed chamber and delivering 0.25 mL of acetaldehyde in 10.5 L chamber. Mice remained in the chamber for two treatments of 20 minutes.

Biochemical Studies In Rats and Mice. Protein was isolated from rat paw tissue at 3 hours after treatment or from liver tissue of mutant or wild type mice. Tissues were homogenized in buffer containing (Hepes 10 mM, NaCl 0.9%, EGTA 1 mM, DTPA 100 μM, Triton-X 1%, Protease and Phosphatase inhibitors (AEBSF, Aprotinin, Bestatin, E-64, Leupeptin, Pepstatin A, Sodium orthovanadate, Sodium molybdate, Sodium tartrate, Imidazole, Cantharidin, (−)-p-Bromolevamisole oxalate and Calyculin A). The samples were centrifuged at 700 g for 5 min at 4° C. Mitochondrial fraction from liver was obtained as previously described (Chen, et al. (2008) Activation of aldehyde dehydrogenase-2 reduces ischemic damage to the heart. Science 321, 1493-1495; Sun, L., et al. ALDH2 activator inhibits increased myocardial infarction injury by nitroglycerin tolerance. Sci Transl Med 3, 107ra111). Activation of aldehyde dehydrogenase-2 reduces ischemic damage to the heart. Science 2008; 321:1493-5). The protein concentration was determined in the supernatants by using Bradford (Bradford, M. M. (1976). A rapid and sensitive method for the quantitation of microgram quantities of protein utilizing the principle of protein-dye binding. Anal Biochem 72, 248-254).

Aldehyde dehydrogenase 2 enzymatic measurement. ALDH2 enzymatic activity was determined as previously described (Chen C H, et al. Activation of aldehyde dehydrogenase-2 reduces ischemic damage to the heart. Science 2008; 321:1493-5; (Sun, L., et al. ALDH2 activator inhibits increased myocardial infarction injury by nitroglycerin tolerance. Sci Transl Med 3, 107ra111). Briefly, the assay was carried out at 25° C. in 50 mM sodium pyrophosphate buffer, pH=9.5, with activity determined spectrophotometrically by monitoring the reductive reaction of NAD+ to NADH at A340 nm after the addition of the substrate 10 mM acetaldehyde. Protein (400 μg) isolated from rat paw tissue or liver tissue of mutant or wild type mice (1.5 mg) were used. To start the reaction, 2.5 mM NAD was added and the NADH accumulation was monitored for 10 min with measurements being taken every 10 s, with reaction expressed as pmol NADH/min/mg protein. This was performed as previously described. Alda-1 (40 mM) was added to specific groups at 3 min to determine the effect of Alda-1 on wild type mice and ALDH2*2 mice. DTT (50 mM) was added to the reaction.

Western blot analysis. Western blot was performed as described (Chen C H, et al., (2008) Activation of aldehyde dehydrogenase-2 reduces ischemic damage to the heart. Science 321: 1493-1495). For 4-hydroxynonenal (4-HNE) protein adduct detection, we used an antibody against the reductively stabilized 4-HNE amino acid adduct (Alpha Diagnostic Intl, 1:1000). For mast cell chymase and neutrophil elastase detection antibodies from Santa Cruz Biotechnology, 1:500 were used. Quantification analysis of blots was performed with Image J software, using GAPDH as a loading control.

Thiobarbituric acid-reactive substance assay. Thiobarbituric acid-reactive substance (TBARS) was measured using an Oxi-Tek TBARS assay kit (ZeptoMetrix, Buffalo, N.Y.). In brief, 100 μL of plantar homogenates were mixed with 100 μl sodium dodecyl sulfonate solution. TBA/buffer reagent was prepared by mixing 0.5 g thiobarbituric acid with 50 ml acetic acid and 50 ml NaOH. TBA/buffer reagent (2.5 ml) was added to 200 μL sample/sodium dodecyl sulfonate mixture and incubated at 95° C. in capped tubes for 60 min. The samples were cooled to room temperature in an ice bath for 10 min and centrifuged at 3,000 g for 15 min. The supernatants were removed, and fluorescence intensity was measured in semi-microcuvettes in a fluorometer (Bio-Rad Laboratories, Hercules, Calif.). The concentration of TBARS was expressed in pmol/mg protein by interpolation from a standard curve of malondialdehyde at 0-200 pmol concentrations. The results are expressed as percent control.

Immunohistochemistry. Animals were anesthetized with ketamine (90 mg/kg) and xylazine (15 mg/kg) after 3 hours of the experimental protocol. Subsequently, animals were perfused with 4% paraformaldehyde (PFA) in 0.1 M phosphate buffer (PB, pH 7.4). Spinal cord sections (L4-L6) were removed, post-fixed for 4 h in PFA (4%), and transferred to a 30% sucrose solution in PB to ensure cryoprotection. Spinal cords were sectioned (10 μm) on a cryostat and displayed on histological glass slides. The sections were immunostained for early growth response-1 gene (EGR1) expression, using a rabbit polyclonal antibody (Santa Cruz Biotechnology 1:500) in PB containing 0.3% Triton X-100 and 5% normal donkey serum. Incubations with primary antibody were conducted overnight at 24° C. The sections were then washed in PB and incubated with a biotinylated donkey anti-rabbit serum (Vector, Burlingame 1:200) in PB for 2 h at 24° C. The sections were washed again in PB and incubated with the avidin-biotin-peroxidase complex (ABC Elite, Vector Labs, USA). The sections were then reacted with 0.05% 3,3-diaminobenzidine and 0.01% hydrogen peroxide in PB. Intensification was conducted with 0.05% osmium tetroxide in water. The sections were dehydrated, cleared and mounted on a cover-slip. Normal rat serum served as control. Digital images of light microscopy were collected and cells with positive EGR were counted.

Figures 1A, 1B, 1C:
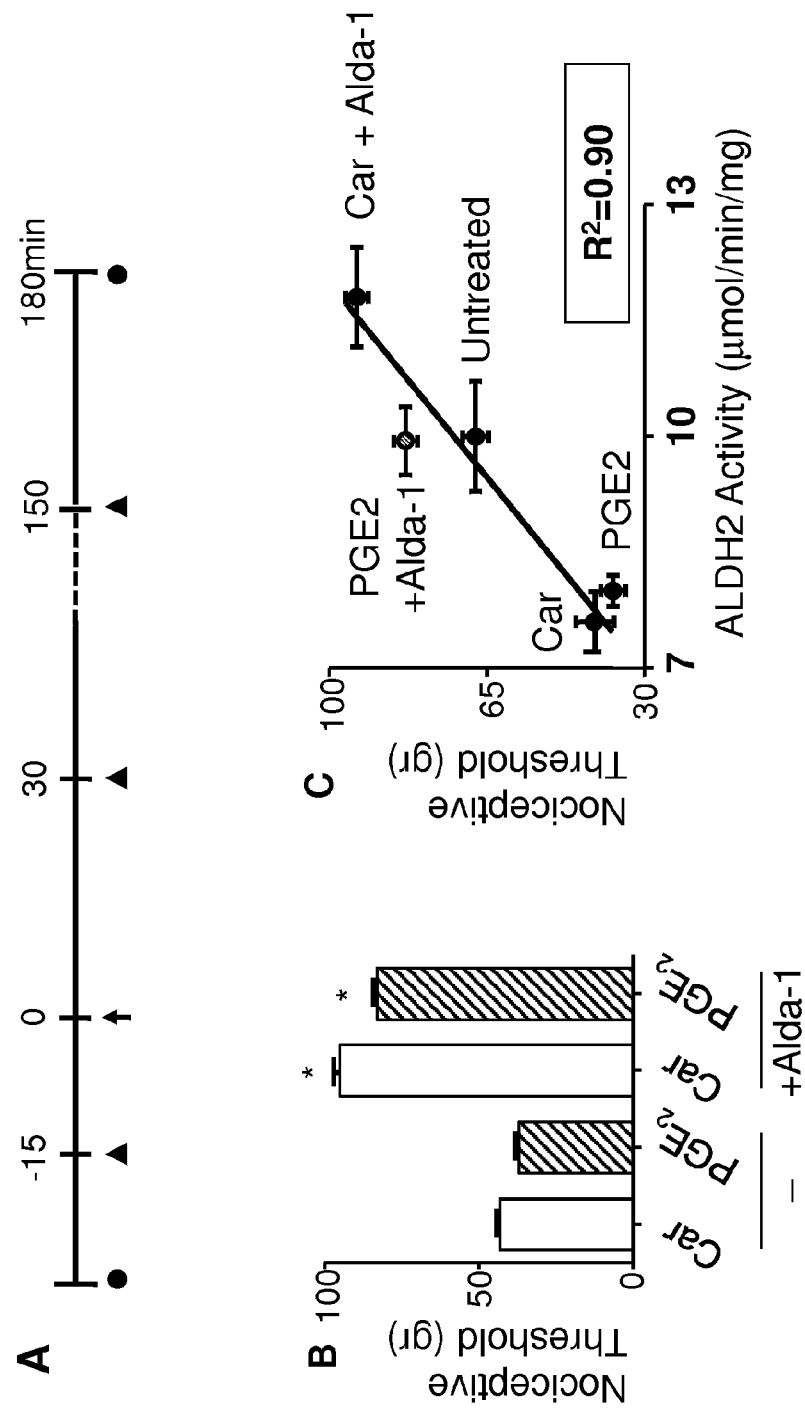
FIG. 1 demonstrates nociceptive behavior in rats and mice following treatment with Alda-1. A. Experimental protocol: Nociceptive threshold testing (closed circles) using Randall-Selitto paw pressure, in rats, and von Frey hairs, in mice, evaluated at baseline and 3 hours after inflammatory insult. Arrowheads indicate treatment either of vehicle or the ALDH2 activator, Alda-1 (2 mg/kg, subcutaneously). At time zero (arrow) the inflammatory insult of either carrageenan (mice and rat studies) or for prostaglandin E2 (rat studies only) was given to the right paw. B. Nociceptive threshold in rats subjected to either carrageenan (open bars) or prostaglandin E2 (PGE2, hashed bars) pro-inflammatory insults. Alda-1 treatment significantly increased nociceptive threshold for both insults. Average of baseline threshold is represented as a dotted line. C. Nociceptive threshold significantly correlated with the level of ALDH2 activity, as measured in paw tissue homogenate; $R^2=0.90$. (n=6/group, *P<0.001.) Error bars represent mean±SEM. D. Nociceptive threshold in mice was assessed blinded by using a scoring scale (2=no response, 1=withdrawal from stimulus, 0=immediate withdrawal from stimulus with licking or flinching) 3 hours after the inflammatory insult. ALDH2*1/*2 mutant mice (red bars) displayed a lower threshold to acute carrageenan-induced inflammation as compared to wild type mice (blue bars). Baseline threshold for each filament is provided in FIG. 6. E. Nociceptive threshold in mice after 1.20 gram von Frey hair stimulus in ALDH2 wild type (WT) and ALDH2 *1/*2 heterozygous mice treated with Alda-1 or vehicle. Alda-1 significantly increased pain threshold for both wild type and ALDH2 *1/*2 treated mice. Average of baseline threshold is represented as a dotted line. (n=6-7/group; *P<0.001 for mouse studies.

Statistical analysis. Data are expressed as mean±SEM. Analysis of variance (ANOVA) with Tukey post-hoc analysis was used for behavioral pain studies and biochemical analysis. For FIG. 1C, linear regression analysis and Pearson's correlation testing were used to assess concordance. A value of at least $p<0.05$ was considered significant Results To determine how ALDH2 activity may regulate nociception, we used the selective small molecule activator of ALDH2, Alda-1, in rats subjected to either a carrageenan or prostaglandin E2 insult to the right hind paw (Protocol; FIG. 1A; the performer of the behavioral experiments was blinded to the drugs given). Alda-1 increased nociceptive threshold by 2 fold in both the carrageenan- and prostaglandin E2-induced nociception models (FIG. 1B). ALDH activity measured in the paw tightly correlated with nociceptive threshold (R2=0.90, FIG. 1C).

If ALDH2 activation is required to reduce the threshold for nociception, we predicted the decreased ALDH2 activity will increase nociception. To test this hypothesis, we generated knock-in mice carrying the inactivating Lys487 point mutation, identical to the denoted ALDH2*2 mutation found in 0.54 billion Han Chinese (Brooks P J, et al., (2009) The alcohol flushing response: an unrecognized risk factor for esophageal cancer from alcohol consumption. PLoS Med 6: e50). See FIG. 5A. ALDH2 protein levels were similar between ALDH2 and ALDH2*2 mice (FIG. 5B). To confirm that the mutant mice mimic the human phenotype, we challenged them with ethanol and determined blood acetaldehyde levels. Similar to human heterozygotes (ALDH2 * 1/*2) (Yokoyama A, et al., (2008) Salivary acetaldehyde concentration according to alcoholic beverage consumed and aldehyde dehydrogenase-2 genotype. Alcoholism, clinical and experimental research 32: 1607-1614), heterozygote ALDH2 *1/*2 mice accumulated 5-fold higher acetaldehyde levels as compared with wild type ALDH2 mice (FIG. 5C).

Figures 1D, 1E:
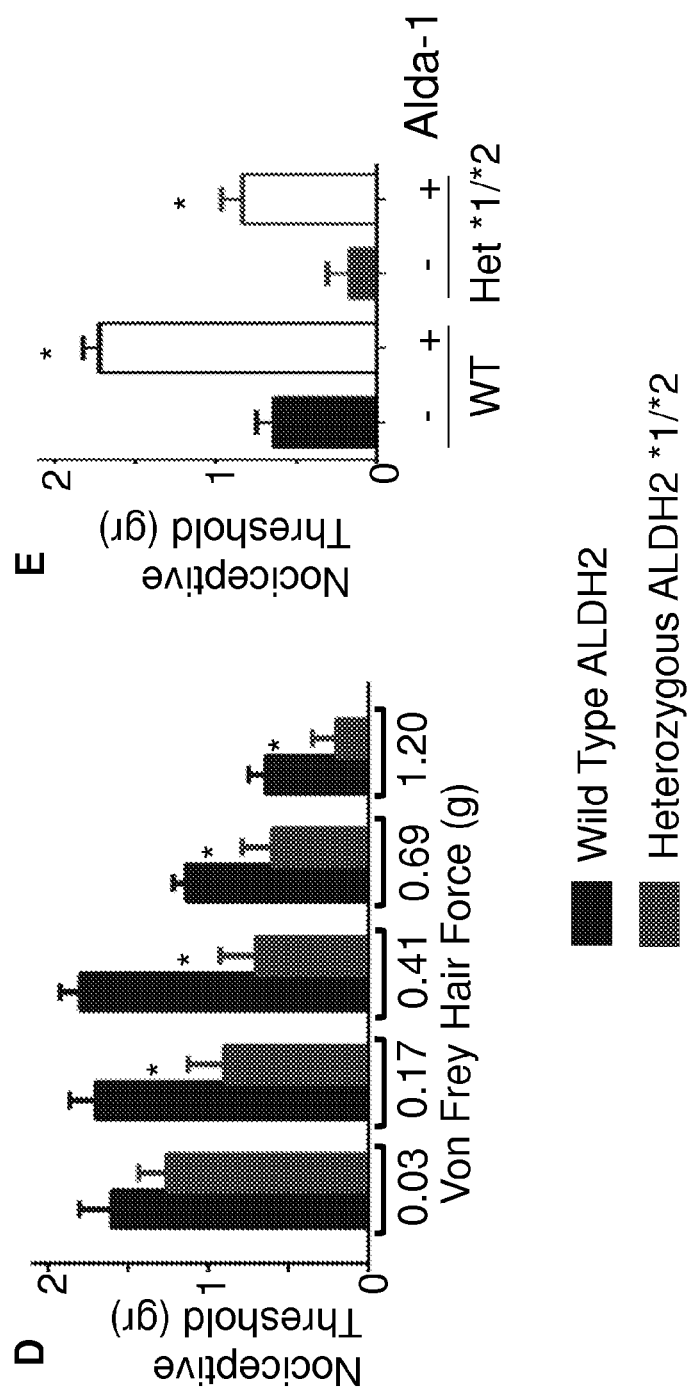

We next tested the ALDH2 *1/*2 heterozygous mice in a carrageenan-induced acute pain model (Protocol, FIG. 1A, the performer was blinded to mouse genotype and drugs given). ALDH2 heterozygous mice displayed more profound hyperalgesia in this acute inflammatory pain model as compared with ALDH2 wild type mice (FIG. 1D). The ALDH2 activator Alda-1 reduced the response to the nociceptive stimulus in the heterozygous ALDH2 *1/*2 mice, bringing the response to wild type levels (FIG. 1E, FIG. 8) Further, we found that Alda-1 reduced nociception in wild type mice, doubling the nociceptive threshold relative to the vehicle-treated mice (FIG. 1E). In order to evaluate the genetic effects on motor activity an open field test was performed. No differences were detected in frequencies of locomotion (ALDH2 wild type mice=54±3 and ALDH2 * 1/*2 heterozygous mice=57±1 units entered) and rearing (ALDH2 wild type mice=6±1 and ALDH2 *1/*2 heterozygous mice 7±1 rearings) (FIG. 7)

Carrageenan-induced inflammation and edema appeared unaltered by Alda-1 treatment (FIG. 2A and B). Carrageenan administration caused a ~30% increase in paw diameter as compared to the untreated contralateral paw of vehicle-treated rats, with the increase unaffected by Alda-1 treatment (FIG. 2A). Furthermore, markers of inflammation, including mast cell chymase (FIG. 2B) and neutrophil elastase (267±61 versus 220±26), increased equally in the vehicle-treated and Alda-1-treated carrageenan groups. In contrast, we observed that early growth response protein 1 (EGR1) levels, a central nervous system marker of hyperalgesia (Rahman O I, et al. (2002) Differential effects of NMDA and AMPA/KA receptor antagonists on c-Fos or Zif/268 expression in the rat spinal dorsal horn induced by noxious thermal or mechanical stimulation, or formalin injection. Neurosci Res 43: 389-399), in the L4-6 spinal cord level increased ~5 fold, which was brought back to basal levels by Alda-1 treatment (FIG. 2C).

We reasoned that if ALDH2 activity is critical for nociception, that aldehydic load will increase in the carrageenan-treated rats. We found that 4-HNE-protein adducts and malondialdehyde (MDA) levels were elevated in the inflamed paw, and the levels reduced by Alda-1 treatment (FIG. 2D and 2E). To our surprise, we also detected acetaldehyde in paws subjected to carrageenan-induced hyperalgesia, and Alda-1 treatment decreased the level of acetaldehyde by ~50% (FIG. 2F).

Since acetaldehyde accumulated in the paw during the carrageenan-induced inflammatory insult, we determined whether acetaldehyde further exacerbates hyperalgesia in animals in which ALDH2 activity is impaired. Blood acetaldehyde increased ~50 fold higher (to 325±37μM) than the untreated levels in ALDH2 *1*2 heterozygotic mice subjected to acetaldehyde vapors (FIG. 5C). We found profound hyperalgesia in mice given acetaldehyde after the carrageenan-induced insult (50 μg) compared to carrageenan alone (FIG. 2G). Moreover, the effect was reversed when Alda-1 was given (FIG. 2G).

Figure 3:
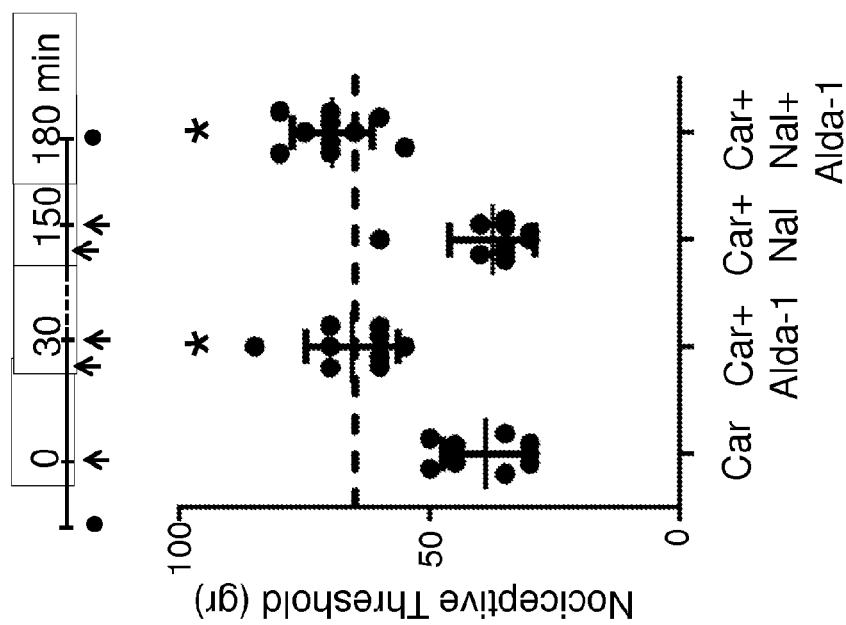
FIG. 3 illustrates the effect of Alda-1 on nociceptive threshold when given after an inflammatory insult. Alda-1 given 30 and 150 minutes after carrageenan significantly increased nociceptive threshold as assessed by Randall-Selitto method (red arrows, Alda-1 or vehicle treatment, 2 mg/kg subcutaneously; n=9/group, *P<0.0001). Naloxone (Nal, 1 mg/kg) or vehicle was given subcutaneously (green arrows) 10 minutes before each Alda-1 treatment. Naloxone treatment had no effect on nociceptive threshold, with or without Alda-1 (n=9/group, *P<0.0001). Error bars represent mean±SEM.

Importantly, Alda-1 increased the nociceptive threshold even when injected after carrageenan, and the effect was not blunted in the presence of the opioid receptor antagonist, naloxone (FIG. 3A). Thus, the beneficial effect of ALDH2 activators is not limited to prophylactic use and can be given even after an insult.

Figure 4:
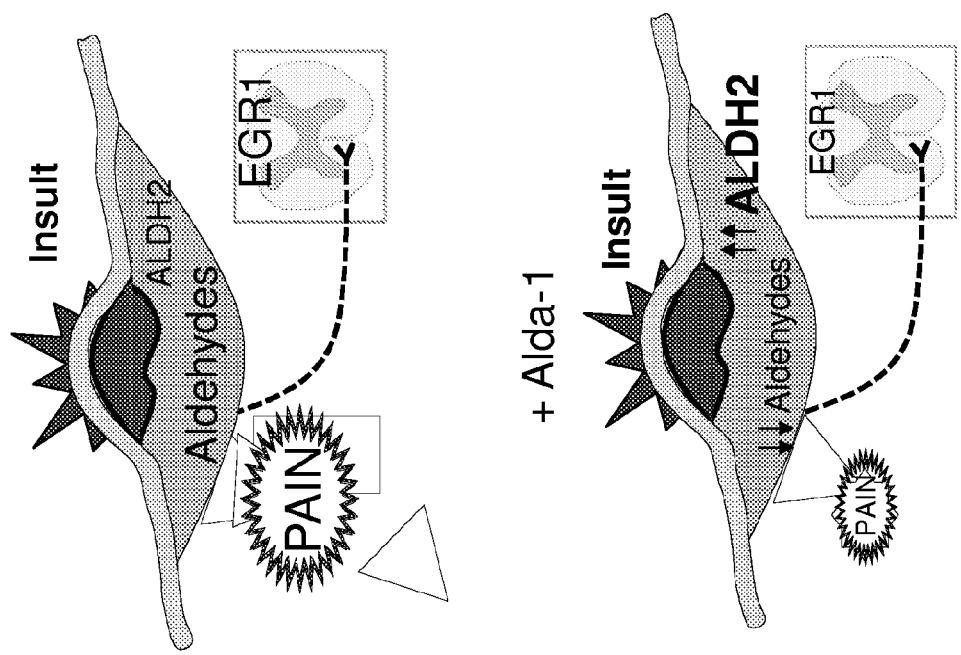
FIG. 4 provides a schematic summary of findings. After an insult, an increase of aldehydes occurs, elevating the marker of hyperalgesia, EGR1, in the spinal cord. Alda-1, by increasing the activity of the mitochondrial enzyme, ALDH2, reverses the pain sensation by reducing aldehydic load, limiting changes in EGR1 and providing analgesia.

Together, our study demonstrates that ALDH2 reduces nociception independent of inflammation by enhancing the catalysis of reactive aldehydes (FIG. 4). As such, ALDH2 activators, such as Alda-1, may represent a new therapeutic for pain. Alda-1 is also more effective than atenolol or celecoxib in reducing carrageenan-induced hyperalgesia when comparing to our previous publication using the same rat hyperalgesia model (Chacur et al, 2003). Moreover, we also previously showed that Alda-1 treatment has a number of cardiovascular benefits, including reducing infarct size and arrhythmias after acute myocardial infarction (Chen C H, et al., (2008) Activation of aldehyde dehydrogenase-2 reduces ischemic damage to the heart. Science 321: 1493-1495; Koda K, et al., (2010) Aldehyde dehydrogenase activation prevents reperfusion arrhythmias by inhibiting local renin release from cardiac mast cells. Circulation 122: 771-781).

Genetic mutations previously reported to regulate pain sensation are limited to small familial subsets of the human population (Cox J J, et al., (2006) An SCN9A channelopathy causes congenital inability to experience pain. Nature 444: 894-898; Kremeyer B, et al., (2010) A gain-of-function mutation in TRPA1 causes familial episodic pain syndrome. Neuron 66: 671-680) and to rare point mutations in ion channels (Emery E C, et al., (2011) HCN2 ion channels play a central role in inflammatory and neuropathic pain. Science 333: 1462-1466; Sorge R E, et al., (2012) Genetically determined P2X7 receptor pore formation regulates variability in chronic pain sensitivity. Nat Med 18: 595-599). Our findings suggest that the ALDH2 point mutation ALDH2*2, present in 40% of East Asian populations, may cause these people to have lower pain thresholds. This may explain prior findings that Asians have a lower pain tolerance than other ethnicities (Chan M Y, et al., (2013) Ethnic differences in physical pain sensitivity: Role of acculturation. Pain 154: 119-123; Rowell L N, et al., (2011) Asians differ from non-Hispanic Whites in experimental pain sensitivity. Eur J Pain 15: 764-771; Wang H, et al., (2010) Ethnic differences in pain, itch and thermal detection in response to topical capsaicin: African Americans display a notably limited hyperalgesia and neurogenic inflammation. Br J Dermatol 162: 1023-1029; Woodrow K M, et al., (1972) Pain tolerance: differences according to age, sex and race. Psychosom Med 34: 548-556). Since Alda-1 also corrects ALDH2 inactivity of the mutant ALDH2*2 (Perez-Miller et al, 2010), such a compound may in particular benefit the East Asian population.

Our study identified ALDH2 as a new regulator of acute nociception in rodents. We found that ALDH2 activation in wild type and in ALDH2*2 mutant mice results in increased nociceptive threshold without affecting the inflammatory response. This data indicate that activators of ALDH2, such as Alda-1, will be a novel therapeutic drug class to reduce pain independent of opioid-receptor signaling and likely without cardiovascular complications.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating hyperalgesia in an individual, comprising:
   administering to the individual an effective amount of an ALDH2 agonist, wherein the ALDH2 agonist is Alda-1 or ALDA-44.

2. The method according to claim 1, wherein the ALDH2 agonist is administered after the onset of pain.

3. The method according to claim 1, wherein the individual is a human.

4. The method according to claim 3, wherein the individual has a hypomorphic mutation in ALDH2.

5. The method according to claim 4, wherein the mutation is ALDH2*2.

6. A method of decreasing hyperalgesia in an individual, comprising:
   administering to the individual an effective amount of an ALDH2 agonist, wherein the ALDH2 agonist is Alda-1 or ALDA-44.

7. The method according to claim 6, wherein the ALDH2 agonist is administered prior to the onset of pain.

8. The method according to claim 6, wherein the individual has a hypomorphic mutation in ALDH2.

9. The method according to claim 8, wherein the mutation is ALDH2*2.

* * * * *